United States Patent
Larson et al.

(10) Patent No.: US 9,636,165 B2
(45) Date of Patent: *May 2, 2017

(54) SYSTEMS AND METHODS FOR MEASURING TISSUE IMPEDANCE THROUGH AN ELECTROSURGICAL CABLE

(71) Applicant: COVIDIEN LP, Mansfield, MA (US)

(72) Inventors: Eric J. Larson, Broomfield, CO (US); Carolyn G. Ford, Louisville, CO (US); Alexander M. Waskiewicz, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 520 days.

This patent is subject to a terminal disclaimer.

(21) Appl. No.: 14/181,114

(22) Filed: Feb. 14, 2014

(65) Prior Publication Data

US 2015/0032099 A1 Jan. 29, 2015

Related U.S. Application Data

(60) Provisional application No. 61/859,601, filed on Jul. 29, 2013, provisional application No. 61/859,624, filed on Jul. 29, 2013.

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1442* (2013.01); *A61B 18/16* (2013.01);
(Continued)

(58) Field of Classification Search
CPC ...... A61N 1/3962; A61N 1/39; A61N 1/3906; A61N 1/3912; A61N 1/3937; A61N 1/3943; A61B 18/1233; A61B 2018/1233
See application file for complete search history.

(56) References Cited

U.S. PATENT DOCUMENTS 1,787,709 A 1/1931 Wappler
1,813,902 A 7/1931 Bovie
(Continued)

FOREIGN PATENT DOCUMENTS

DE 179607 C 3/1905
DE 390937 C 3/1924
(Continued)

OTHER PUBLICATIONS

US 6,878,148, 04/2005, Goble et al. (withdrawn)
(Continued)

*Primary Examiner* — Joseph Stoklosa
*Assistant Examiner* — Eunhwa Kim

(57) ABSTRACT

The electrosurgical systems and methods of the present disclosure include a tissue resistance measurement system that compensates for capacitive parasitics in a cable connecting an electrosurgical generator to and electrosurgical cable to estimate the real resistance of a tissue load. The electrosurgical generator includes an output stage coupled to an electrical energy source and generates electrosurgical energy. The electrosurgical generator includes a plurality of sensors sensing a voltage and current of the electrosurgical energy and a controller controlling the output stage. The controller includes a calculator that calculates a real part of an impedance based on the sensed voltage and current, an estimator that estimates a resistance of the tissue using a solution to a quadratic equation that is a function of the real part of the impedance, and a control signal generator configured to generate a control signal for the output stage based on the resistance of the tissue.

20 Claims, 8 Drawing Sheets

(51) Int. Cl.
  *A61B 18/16* (2006.01)
  *A61B 18/00* (2006.01)
(52) U.S. Cl.
  CPC ............... *A61B 2018/00577* (2013.01); *A61B 2018/00607* (2013.01); *A61B 2018/00875* (2013.01)

(56) References Cited

U.S. PATENT DOCUMENTS

| | | |
|---|---|---|
| 1,841,968 A | 1/1932 | Lowry |
| 1,863,118 A | 6/1932 | Liebel |
| 1,945,867 A | 2/1934 | Rawls |
| 2,693,106 A | 6/1951 | Henry |
| 2,827,056 A | 3/1958 | Degelman |
| 2,849,611 A | 8/1958 | Adams |
| 2,883,198 A | 4/1959 | Narumi |
| 3,001,132 A | 9/1961 | Britt |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hiltebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gonser |
| 4,247,815 A | 1/1981 | Larsen et al. |
| 4,271,837 A | 6/1981 | Schuler |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,524,444 A | 6/1985 | Efron et al. |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,580,575 A | 4/1986 | Birnbaum et al. |
| 4,582,057 A | 4/1986 | Auth et al. |
| 4,586,120 A | 4/1986 | Malik et al. |
| 4,590,934 A | 5/1986 | Malis et al. |

(56) References Cited

U.S. PATENT DOCUMENTS

| | | |
|---|---|---|
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,754,757 A | 7/1988 | Feucht |
| 4,767,999 A | 8/1988 | VerPlanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan, Sr. et al. |
| 4,903,696 A | 2/1990 | Stasz et al. |
| 4,907,589 A | 3/1990 | Cosman |
| 4,922,210 A | 5/1990 | Flachenecker et al. |
| 4,925,089 A | 5/1990 | Chaparro et al. |
| 4,931,047 A | 6/1990 | Broadwin et al. |
| 4,931,717 A | 6/1990 | Gray et al. |
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,057,105 A | 10/1991 | Malone et al. |
| 5,067,953 A | 11/1991 | Feucht |
| 5,075,839 A | 12/1991 | Fisher et al. |
| 5,078,153 A | 1/1992 | Nordlander et al. |
| 5,087,257 A | 2/1992 | Farin et al. |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker et al. |
| 5,113,116 A | 5/1992 | Wilson |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke et al. |
| 5,196,009 A | 3/1993 | Kirwan, Jr. |
| 5,201,900 A | 4/1993 | Nardella |
| 5,207,691 A | 5/1993 | Nardella |
| 5,216,338 A | 6/1993 | Wilson |
| 5,230,623 A | 7/1993 | Guthrie et al. |
| 5,233,515 A | 8/1993 | Cosman |
| 5,234,427 A | 8/1993 | Ohtomo et al. |
| 5,244,462 A | 9/1993 | Delahuerga et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin et al. |
| 5,269,780 A | 12/1993 | Roos |
| 5,271,413 A | 12/1993 | Dalamagas et al. |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia et al. |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman et al. |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,354,325 A | 10/1994 | Chive et al. |
| 5,364,392 A | 11/1994 | Warner et al. |
| 5,369,567 A | 11/1994 | Furuta et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson et al. |
| 5,383,876 A | 1/1995 | Nardella |
| 5,383,917 A | 1/1995 | Desai et al. |
| 5,385,148 A | 1/1995 | Lesh et al. |
| 5,396,194 A | 3/1995 | Williamson et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A * | 6/1995 | Matsunaga ........ A61B 18/1206 324/142 |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson et al. |
| 5,433,739 A | 7/1995 | Sluijter et al. |
| 5,436,566 A | 7/1995 | Thompson et al. |
| 5,438,302 A | 8/1995 | Goble |
| 5,443,462 A | 8/1995 | Hannant |
| 5,443,463 A | 8/1995 | Stern et al. |
| 5,445,635 A | 8/1995 | Denen et al. |
| 5,445,638 A | 8/1995 | Rydell et al. |
| 5,448,466 A | 9/1995 | Erckert |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |

(56) References Cited

U.S. PATENT DOCUMENTS

| | | |
|---|---|---|
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,485,312 A | 1/1996 | Horner et al. |
| 5,496,312 A | 3/1996 | Klicek |
| 5,496,313 A | 3/1996 | Gentelia et al. |
| 5,496,314 A | 3/1996 | Eggers |
| 5,498,261 A | 3/1996 | Strul |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa et al. |
| 5,540,684 A | 7/1996 | Hassler, Jr. |
| 5,541,376 A | 7/1996 | Ladtkow et al. |
| 5,542,916 A | 8/1996 | Hirsch et al. |
| 5,545,161 A | 8/1996 | Imran |
| 5,554,172 A | 9/1996 | Horner et al. |
| 5,556,396 A | 9/1996 | Cohen et al. |
| 5,558,671 A | 9/1996 | Yates |
| 5,559,688 A | 9/1996 | Pringle |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,596,995 A | 1/1997 | Sherman et al. |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,633,578 A | 5/1997 | Eggers et al. |
| 5,640,113 A | 6/1997 | Hu |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,675,609 A | 10/1997 | Johnson |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |
| 5,693,042 A | 12/1997 | Boiarski et al. |
| 5,693,078 A | 12/1997 | Desai et al. |
| 5,693,082 A | 12/1997 | Warner et al. |
| 5,694,304 A | 12/1997 | Telefus et al. |
| 5,695,494 A | 12/1997 | Becker |
| 5,696,441 A | 12/1997 | Mak et al. |
| 5,697,925 A | 12/1997 | Taylor |
| 5,697,927 A | 12/1997 | Imran et al. |
| 5,702,386 A | 12/1997 | Stern et al. |
| 5,702,429 A | 12/1997 | King |
| 5,707,369 A | 1/1998 | Vaitekunas et al. |
| 5,712,772 A | 1/1998 | Telefus et al. |
| 5,713,896 A | 2/1998 | Nardella |
| 5,718,246 A | 2/1998 | Vona |
| 5,720,742 A | 2/1998 | Zacharias |
| 5,720,744 A | 2/1998 | Eggleston et al. |
| 5,722,975 A | 3/1998 | Edwards et al. |
| 5,729,448 A | 3/1998 | Haynie et al. |
| 5,733,281 A | 3/1998 | Nardella |
| 5,735,846 A | 4/1998 | Panescu et al. |
| 5,738,683 A | 4/1998 | Osypka |
| 5,743,900 A | 4/1998 | Hara |
| 5,743,903 A | 4/1998 | Stern et al. |
| 5,749,869 A | 5/1998 | Lindenmeier et al. |
| 5,749,871 A | 5/1998 | Hood et al. |
| 5,755,715 A | 5/1998 | Stern et al. |
| 5,762,609 A | 6/1998 | Benaron et al. |
| 5,766,153 A | 6/1998 | Eggers et al. |
| 5,766,165 A | 6/1998 | Gentelia et al. |
| 5,769,847 A | 6/1998 | Panescu et al. |
| 5,772,659 A | 6/1998 | Becker et al. |
| 5,777,519 A | 7/1998 | Simopoulos |
| 5,788,688 A | 8/1998 | Bauer et al. |
| 5,792,138 A | 8/1998 | Shipp |
| 5,797,902 A | 8/1998 | Netherly |
| 5,797,941 A | 8/1998 | Schulze et al. |
| 5,807,253 A | 9/1998 | Dumoulin et al. |
| 5,810,804 A | 9/1998 | Gough et al. |
| 5,814,092 A | 9/1998 | King |
| 5,817,091 A | 10/1998 | Nardella et al. |
| 5,817,093 A | 10/1998 | Williamson, IV et al. |
| 5,820,568 A | 10/1998 | Willis |
| 5,827,271 A | 10/1998 | Buysse et al. |
| 5,830,212 A | 11/1998 | Cartmell et al. |
| 5,831,166 A | 11/1998 | Kozuka et al. |
| 5,836,909 A | 11/1998 | Cosmescu |
| 5,836,943 A | 11/1998 | Miller, III |
| 5,836,990 A | 11/1998 | Li |
| 5,843,019 A | 12/1998 | Eggers et al. |
| 5,843,075 A | 12/1998 | Taylor |
| 5,846,236 A | 12/1998 | Lindenmeier et al. |
| 5,849,010 A | 12/1998 | Wurzer et al. |
| 5,853,409 A | 12/1998 | Swanson et al. |
| 5,860,832 A | 1/1999 | Wayt et al. |
| 5,865,788 A | 2/1999 | Edwards et al. |
| 5,868,737 A | 2/1999 | Taylor et al. |
| 5,868,739 A | 2/1999 | Lindenmeier et al. |
| 5,868,740 A | 2/1999 | LeVeen et al. |
| 5,871,481 A | 2/1999 | Kannenberg et al. |
| 5,891,142 A | 4/1999 | Eggers et al. |
| 5,893,848 A | 4/1999 | Negus et al. |
| 5,897,552 A | 4/1999 | Edwards et al. |
| 5,906,614 A | 5/1999 | Stern et al. |
| 5,908,444 A | 6/1999 | Azure |
| 5,913,882 A | 6/1999 | King |
| 5,921,982 A | 7/1999 | Lesh et al. |
| 5,925,070 A | 7/1999 | King et al. |
| 5,931,835 A | 8/1999 | Mackey |
| 5,931,836 A | 8/1999 | Hatta et al. |
| 5,935,124 A | 8/1999 | Klumb et al. |
| 5,936,446 A | 8/1999 | Lee |
| 5,938,690 A | 8/1999 | Law et al. |
| 5,944,553 A | 8/1999 | Yasui et al. |
| 5,948,007 A | 9/1999 | Starkebaum et al. |
| 5,951,545 A | 9/1999 | Schilling et al. |
| 5,951,546 A | 9/1999 | Lorentzen |
| 5,954,686 A | 9/1999 | Garito et al. |
| 5,954,717 A | 9/1999 | Behl et al. |
| 5,954,719 A | 9/1999 | Chen et al. |
| 5,957,961 A | 9/1999 | Maguire et al. |
| 5,957,969 A | 9/1999 | Warner et al. |
| 5,959,253 A | 9/1999 | Shinchi |
| 5,961,344 A | 10/1999 | Rosales et al. |
| 5,961,871 A | 10/1999 | Bible et al. |
| 5,964,746 A | 10/1999 | McCary |
| 5,971,980 A | 10/1999 | Sherman |
| 5,971,981 A | 10/1999 | Hill et al. |
| 5,976,128 A | 11/1999 | Schilling et al. |
| 5,983,141 A | 11/1999 | Sluijter et al. |
| 5,999,848 A | 12/1999 | Gord et al. |
| 6,002,968 A | 12/1999 | Edwards |

(56) References Cited

U.S. PATENT DOCUMENTS

| | | | |
|---|---|---|---|
| 6,007,532 A | 12/1999 | Netherly | |
| 6,010,499 A | 1/2000 | Cobb | |
| 6,013,074 A | 1/2000 | Taylor | |
| 6,014,581 A | 1/2000 | Whayne et al. | |
| 6,017,338 A | 1/2000 | Brucker et al. | |
| 6,017,354 A | 1/2000 | Culp et al. | |
| 6,022,346 A | 2/2000 | Panescu et al. | |
| 6,022,347 A | 2/2000 | Lindenmeier et al. | |
| 6,033,399 A | 3/2000 | Gines | |
| 6,039,731 A | 3/2000 | Taylor et al. | |
| 6,039,732 A | 3/2000 | Ichikawa et al. | |
| 6,041,260 A | 3/2000 | Stern et al. | |
| 6,044,283 A | 3/2000 | Fein et al. | |
| 6,045,527 A | 4/2000 | Appelbaum et al. | |
| 6,053,910 A | 4/2000 | Fleenor | |
| 6,053,912 A | 4/2000 | Panescu et al. | |
| 6,055,458 A | 4/2000 | Cochran et al. | |
| 6,056,745 A | 5/2000 | Panescu et al. | |
| 6,056,746 A | 5/2000 | Goble et al. | |
| 6,058,325 A * | 5/2000 | Baura | A61N 1/3943 600/547 |
| 6,059,780 A | 5/2000 | Gough et al. | |
| 6,059,781 A | 5/2000 | Yamanashi et al. | |
| 6,063,075 A | 5/2000 | Mihori | |
| 6,063,078 A | 5/2000 | Wittkampf | |
| 6,066,137 A | 5/2000 | Greep | |
| 6,068,627 A | 5/2000 | Orszulak et al. | |
| 6,074,089 A | 6/2000 | Hollander et al. | |
| 6,074,386 A | 6/2000 | Goble et al. | |
| 6,074,388 A | 6/2000 | Tockweiler et al. | |
| 6,080,149 A | 6/2000 | Huang et al. | |
| 6,088,614 A | 7/2000 | Swanson | |
| 6,089,864 A | 7/2000 | Buckner et al. | |
| 6,090,123 A | 7/2000 | Culp et al. | |
| 6,093,186 A | 7/2000 | Goble | |
| 6,102,497 A | 8/2000 | Ehr et al. | |
| 6,102,907 A | 8/2000 | Smethers et al. | |
| 6,104,248 A | 8/2000 | Carver | |
| 6,106,524 A | 8/2000 | Eggers et al. | |
| 6,113,591 A | 9/2000 | Whayne et al. | |
| 6,113,592 A | 9/2000 | Taylor | |
| 6,113,593 A | 9/2000 | Tu et al. | |
| 6,113,596 A | 9/2000 | Hooven et al. | |
| 6,123,701 A | 9/2000 | Nezhat | |
| 6,123,702 A | 9/2000 | Swanson et al. | |
| 6,132,429 A | 10/2000 | Baker | |
| 6,139,349 A | 10/2000 | Wright | |
| 6,142,992 A | 11/2000 | Cheng et al. | |
| 6,144,937 A | 11/2000 | Ali | |
| 6,155,975 A | 12/2000 | Urich et al. | |
| 6,162,184 A | 12/2000 | Swanson et al. | |
| 6,162,217 A | 12/2000 | Kannenberg et al. | |
| 6,165,169 A | 12/2000 | Panescu et al. | |
| 6,165,173 A | 12/2000 | Kamdar et al. | |
| 6,171,304 B1 | 1/2001 | Netherly et al. | |
| 6,173,713 B1 | 1/2001 | Dawson | |
| 6,183,468 B1 | 2/2001 | Swanson et al. | |
| 6,186,147 B1 | 2/2001 | Cobb | |
| 6,188,211 B1 | 2/2001 | Rincon-Mora et al. | |
| 6,193,713 B1 | 2/2001 | Geistert et al. | |
| 6,197,023 B1 | 3/2001 | Muntermann | |
| 6,200,314 B1 | 3/2001 | Sherman | |
| 6,203,541 B1 | 3/2001 | Keppel | |
| 6,210,403 B1 | 4/2001 | Klicek | |
| 6,216,704 B1 | 4/2001 | Ingle et al. | |
| 6,222,356 B1 | 4/2001 | Taghizadeh-Kaschani | |
| 6,228,078 B1 | 5/2001 | Eggers et al. | |
| 6,228,080 B1 | 5/2001 | Gines | |
| 6,228,081 B1 | 5/2001 | Goble | |
| 6,231,569 B1 | 5/2001 | Bek et al. | |
| 6,232,556 B1 | 5/2001 | Daugherty et al. | |
| 6,235,020 B1 | 5/2001 | Cheng et al. | |
| 6,235,022 B1 | 5/2001 | Hallock et al. | |
| 6,237,604 B1 | 5/2001 | Burnside et al. | |
| 6,238,387 B1 | 5/2001 | Miller, III | |
| 6,238,388 B1 | 5/2001 | Ellman et al. | |
| 6,241,723 B1 | 6/2001 | Heim et al. | |
| 6,241,725 B1 | 6/2001 | Cosman | |
| 6,243,654 B1 | 6/2001 | Johnson et al. | |
| 6,245,061 B1 | 6/2001 | Panescu et al. | |
| 6,245,063 B1 | 6/2001 | Uphoff | |
| 6,245,065 B1 | 6/2001 | Panescu et al. | |
| 6,246,912 B1 | 6/2001 | Sluijter et al. | |
| 6,251,106 B1 | 6/2001 | Becker et al. | |
| 6,254,422 B1 | 7/2001 | Feye-Hohmann | |
| 6,258,085 B1 | 7/2001 | Eggleston | |
| 6,259,937 B1 | 7/2001 | Schulman et al. | |
| 6,261,285 B1 | 7/2001 | Novak et al. | |
| 6,261,286 B1 | 7/2001 | Goble et al. | |
| 6,267,760 B1 | 7/2001 | Swanson | |
| 6,270,497 B1 | 8/2001 | Sekino et al. | |
| 6,273,886 B1 | 8/2001 | Edwards et al. | |
| 6,275,786 B1 | 8/2001 | Daners | |
| 6,287,304 B1 | 9/2001 | Eggers et al. | |
| 6,293,941 B1 | 9/2001 | Strul et al. | |
| 6,293,942 B1 | 9/2001 | Goble et al. | |
| 6,293,943 B1 | 9/2001 | Panescu et al. | |
| 6,296,636 B1 | 10/2001 | Cheng et al. | |
| 6,304,138 B1 | 10/2001 | Johnson | |
| 6,306,131 B1 | 10/2001 | Hareyama et al. | |
| 6,306,134 B1 | 10/2001 | Goble et al. | |
| 6,309,386 B1 | 10/2001 | Bek | |
| 6,322,558 B1 | 11/2001 | Taylor et al. | |
| 6,325,799 B1 | 12/2001 | Goble | |
| 6,329,778 B1 | 12/2001 | Culp et al. | |
| 6,337,998 B1 | 1/2002 | Behl et al. | |
| 6,338,657 B1 | 1/2002 | Harper et al. | |
| 6,341,981 B1 | 1/2002 | Gorman | |
| 6,350,262 B1 | 2/2002 | Ashley | |
| 6,350,263 B1 | 2/2002 | Wetzig et al. | |
| 6,358,245 B1 | 3/2002 | Edwards et al. | |
| 6,364,877 B1 | 4/2002 | Goble et al. | |
| 6,370,408 B1 | 4/2002 | Merchant et al. | |
| 6,371,963 B1 | 4/2002 | Nishtala et al. | |
| 6,383,183 B1 | 5/2002 | Sekino et al. | |
| 6,387,092 B1 | 5/2002 | Burnside et al. | |
| 6,391,024 B1 | 5/2002 | Sun et al. | |
| 6,398,779 B1 | 6/2002 | Buysse et al. | |
| 6,398,781 B1 | 6/2002 | Goble et al. | |
| 6,402,741 B1 | 6/2002 | Keppel et al. | |
| 6,402,742 B1 | 6/2002 | Blewett et al. | |
| 6,402,743 B1 | 6/2002 | Orszulak et al. | |
| 6,402,748 B1 | 6/2002 | Schoenman et al. | |
| 6,409,722 B1 | 6/2002 | Hoey et al. | |
| 6,413,256 B1 | 7/2002 | Truckai et al. | |
| 6,416,509 B1 | 7/2002 | Goble et al. | |
| 6,422,896 B2 | 7/2002 | Aoki et al. | |
| 6,423,057 B1 | 7/2002 | He et al. | |
| 6,424,186 B1 | 7/2002 | Quimby et al. | |
| 6,426,886 B1 | 7/2002 | Goder | |
| 6,427,089 B1 | 7/2002 | Knowlton | |
| 6,428,537 B1 | 8/2002 | Swanson et al. | |
| 6,436,096 B1 | 8/2002 | Hareyama | |
| 6,440,157 B1 | 8/2002 | Shigezawa et al. | |
| 6,451,015 B1 | 9/2002 | Rittman, III et al. | |
| 6,454,594 B2 | 9/2002 | Sawayanagi | |
| 6,458,121 B1 | 10/2002 | Rosenstock et al. | |
| 6,458,122 B1 | 10/2002 | Pozzato | |
| 6,464,689 B1 | 10/2002 | Qin et al. | |
| 6,464,696 B1 | 10/2002 | Oyama et al. | |
| 6,468,270 B1 | 10/2002 | Hovda et al. | |
| 6,468,273 B1 | 10/2002 | Leveen et al. | |
| 6,469,481 B1 | 10/2002 | Tateishi | |
| 6,482,201 B1 | 11/2002 | Olsen et al. | |
| 6,485,487 B1 | 11/2002 | Sherman | |
| 6,488,678 B2 | 12/2002 | Sherman | |
| 6,494,880 B1 | 12/2002 | Swanson et al. | |
| 6,497,659 B1 | 12/2002 | Rafert | |
| 6,498,466 B1 | 12/2002 | Edwards | |
| 6,506,189 B1 | 1/2003 | Rittman, III et al. | |
| 6,508,815 B1 | 1/2003 | Strul et al. | |
| 6,511,476 B2 | 1/2003 | Hareyama | |
| 6,511,478 B1 | 1/2003 | Burnside et al. | |
| 6,514,251 B1 | 2/2003 | Ni et al. | |

(56) References Cited

U.S. PATENT DOCUMENTS

| | | |
|---|---|---|
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,258 B2 | 4/2003 | Fleenor et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton et al. |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Bloom et al. |
| 6,623,423 B2 | 9/2003 | Ozaki et al. |
| 6,626,901 B1 | 9/2003 | Treat et al. |
| 6,629,973 B1 | 10/2003 | Wårdell et al. |
| 6,629,974 B2 | 10/2003 | Penny et al. |
| 6,632,193 B1 | 10/2003 | Davison et al. |
| 6,635,056 B2 | 10/2003 | Kadhiresan et al. |
| 6,635,057 B2 | 10/2003 | Harano et al. |
| 6,645,198 B1 | 11/2003 | Bommannan et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,514 B2 | 11/2003 | Ellman et al. |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda et al. |
| 6,682,527 B2 | 1/2004 | Strul |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim et al. |
| 6,693,782 B1 | 2/2004 | Lash |
| 6,695,837 B2 | 2/2004 | Howell |
| 6,696,844 B2 | 2/2004 | Wong et al. |
| 6,700,076 B2 | 3/2004 | Sun et al. |
| 6,712,813 B2 | 3/2004 | Ellman et al. |
| 6,723,091 B2 | 4/2004 | Goble et al. |
| 6,730,078 B2 | 5/2004 | Simpson et al. |
| 6,730,079 B2 | 5/2004 | Lovewell |
| 6,730,080 B2 | 5/2004 | Harano et al. |
| 6,733,495 B1 | 5/2004 | Bek et al. |
| 6,733,498 B2 | 5/2004 | Paton et al. |
| 6,736,810 B2 | 5/2004 | Hoey et al. |
| 6,740,079 B1 | 5/2004 | Eggers et al. |
| 6,740,085 B2 | 5/2004 | Hareyama et al. |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,775,575 B2 | 8/2004 | Bommannan et al. |
| 6,778,044 B2 | 8/2004 | Fehrenbach et al. |
| 6,783,523 B2 | 8/2004 | Qin et al. |
| 6,784,405 B2 | 8/2004 | Flugstad et al. |
| 6,786,905 B2 | 9/2004 | Swanson et al. |
| 6,788,977 B2 | 9/2004 | Fenn et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham et al. |
| 6,809,508 B2 | 10/2004 | Donofrio |
| 6,818,000 B2 | 11/2004 | Muller et al. |
| 6,819,027 B2 | 11/2004 | Saraf |
| 6,824,539 B2 | 11/2004 | Novak |
| 6,830,569 B2 | 12/2004 | Thompson et al. |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey et al. |
| 6,855,141 B2 | 2/2005 | Lovewell |
| 6,855,142 B2 | 2/2005 | Harano et al. |
| 6,860,881 B2 | 3/2005 | Sturm et al. |
| 6,864,686 B2 | 3/2005 | Novak et al. |
| 6,875,210 B2 | 4/2005 | Refior et al. |
| 6,887,240 B1 | 5/2005 | Lands et al. |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,953,461 B2 | 10/2005 | McClurken et al. |
| 6,958,064 B2 | 10/2005 | Rioux et al. |
| 6,962,587 B2 | 11/2005 | Johnson et al. |
| 6,966,907 B2 | 11/2005 | Goble |
| 6,970,752 B1 | 11/2005 | Lim et al. |
| 6,974,453 B2 | 12/2005 | Woloszko et al. |
| 6,974,463 B2 | 12/2005 | Magers et al. |
| 6,977,495 B2 | 12/2005 | Donofrio |
| 6,979,329 B2 | 12/2005 | Burnside et al. |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 6,997,935 B2 | 2/2006 | Anderson et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,048,687 B1 | 5/2006 | Reuss et al. |
| 7,058,372 B1 | 6/2006 | Pardoen et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,087,054 B2 | 8/2006 | Truckai et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |

(56) References Cited

U.S. PATENT DOCUMENTS

| | | | |
|---|---|---|---|
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,184,820 B2 | 2/2007 | Jersey-Willuhn et al. |
| 7,190,933 B2 | 3/2007 | De Ruijter et al. |
| 7,192,427 B2 | 3/2007 | Chapelon et al. |
| 7,195,627 B2 | 3/2007 | Amoah et al. |
| 7,200,010 B2 | 4/2007 | Broman et al. |
| 7,203,556 B2 | 4/2007 | Daners |
| 7,204,835 B2 | 4/2007 | Latterell et al. |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,241,296 B2 | 7/2007 | Buysse et al. |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,269,034 B2 | 9/2007 | Schlecht |
| 7,276,068 B2 | 10/2007 | Johnson et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | van Zyl |
| 7,311,703 B2 | 12/2007 | Turovskiy et al. |
| 7,316,682 B2 | 1/2008 | Konesky |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,468,499 B2 | 12/2008 | Canini et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,511,472 B1 | 3/2009 | Xia et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,568,619 B2 | 8/2009 | Todd et al. |
| 7,573,693 B2 | 8/2009 | Hornung |
| 7,582,084 B2 | 9/2009 | Swanson et al. |
| 7,621,041 B2 | 11/2009 | Banerji et al. |
| 7,628,786 B2 | 12/2009 | Plaven et al. |
| 7,648,499 B2 | 1/2010 | Orszulak et al. |
| 7,651,492 B2 | 1/2010 | Wham |
| 7,651,493 B2 | 1/2010 | Arts et al. |
| 7,655,003 B2 | 2/2010 | Lorang et al. |
| 7,666,182 B2 | 2/2010 | Klett et al. |
| 7,675,429 B2 | 3/2010 | Cernasov |
| 7,678,105 B2 | 3/2010 | McGreevy et al. |
| 7,722,601 B2 | 5/2010 | Wham et al. |
| 7,731,717 B2 | 6/2010 | Odom et al. |
| 7,736,358 B2 | 6/2010 | Shores et al. |
| 7,736,359 B2 | 6/2010 | McPherson |
| 7,744,593 B2 | 6/2010 | Mihori |
| 7,749,217 B2 | 7/2010 | Podhajsky |
| 7,766,693 B2 | 8/2010 | Sartor et al. |
| 7,766,905 B2 | 8/2010 | Paterson et al. |
| 7,780,662 B2 | 8/2010 | Bahney |
| 7,780,764 B2 | 8/2010 | Baksh |
| 7,794,457 B2 | 9/2010 | McPherson et al. |
| 7,799,020 B2 | 9/2010 | Shores et al. |
| 7,799,026 B2 | 9/2010 | Schechter et al. |
| 7,824,400 B2 | 11/2010 | Keppel |
| 7,834,484 B2 | 11/2010 | Sartor |
| 7,863,841 B2 | 1/2011 | Menegoli et al. |
| 7,863,984 B1 | 1/2011 | Behnke |
| 7,864,129 B2 | 1/2011 | Konishi |
| 7,879,029 B2 | 2/2011 | Jimenez |
| 7,879,033 B2 | 2/2011 | Sartor et al. |
| 7,901,400 B2 | 3/2011 | Wham et al. |
| 7,927,328 B2 | 4/2011 | Orszulak et al. |
| 7,947,039 B2 | 5/2011 | Sartor |
| 7,956,620 B2 | 6/2011 | Gilbert |
| 7,959,626 B2 | 6/2011 | Hong et al. |
| 7,972,328 B2 | 7/2011 | Wham et al. |
| 7,972,332 B2 | 7/2011 | Arts et al. |
| 7,976,544 B2 | 7/2011 | McClurken et al. |
| 8,004,121 B2 | 8/2011 | Sartor |
| 8,012,150 B2 | 9/2011 | Wham et al. |
| 8,025,660 B2 | 9/2011 | Plaven et al. |
| 8,034,049 B2 | 10/2011 | Odom et al. |
| 8,038,676 B2 | 10/2011 | Fischer |
| 8,070,746 B2 | 12/2011 | Orton et al. |
| 8,080,008 B2 | 12/2011 | Wham et al. |
| 8,083,735 B2 | 12/2011 | Morris |
| 8,096,961 B2 | 1/2012 | Orszulak et al. |
| 8,104,596 B2 | 1/2012 | Kim et al. |
| 8,105,323 B2 | 1/2012 | Buysse et al. |
| 8,113,057 B2 | 2/2012 | Orszulak et al. |
| 8,133,218 B2 | 3/2012 | Daw et al. |
| 8,133,222 B2 | 3/2012 | Ormsby |
| 8,147,485 B2 | 4/2012 | Wham et al. |
| 8,152,800 B2 | 4/2012 | Behnke |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,167,875 B2 | 5/2012 | Podhajsky et al. |
| 8,174,267 B2 | 5/2012 | Brannan et al. |
| 8,187,262 B2 | 5/2012 | Orszulak |
| 8,200,317 B2 | 6/2012 | Baxi et al. |
| 8,202,271 B2 | 6/2012 | Orszulak |
| 8,211,100 B2 | 7/2012 | Podhajsky et al. |
| 8,216,219 B2 | 7/2012 | Desinger et al. |
| 8,216,220 B2 | 7/2012 | Jensen et al. |
| 8,216,223 B2 | 7/2012 | Wham et al. |
| 8,226,639 B2 | 7/2012 | Podhajsky et al. |
| 8,231,553 B2 | 7/2012 | Joseph et al. |
| 8,231,614 B2 | 7/2012 | Dunning et al. |
| 8,231,616 B2 | 7/2012 | McPherson et al. |

(56) References Cited

U.S. PATENT DOCUMENTS

| | | | |
|---|---|---|---|
| 8,235,917 B2 | 8/2012 | Joseph et al. | |
| 8,241,278 B2 | 8/2012 | Sartor | |
| 8,242,782 B2 | 8/2012 | Brannan et al. | |
| 8,248,075 B2 | 8/2012 | Brannan et al. | |
| 8,257,349 B2 | 9/2012 | Orszulak | |
| 8,257,350 B2 | 9/2012 | Marion | |
| 8,262,652 B2 | 9/2012 | Podhajsky | |
| 8,267,928 B2 | 9/2012 | Orszulak et al. | |
| 8,267,929 B2 | 9/2012 | Wham et al. | |
| 8,287,528 B2 | 10/2012 | Wham et al. | |
| 8,287,529 B2 | 10/2012 | Orszulak | |
| 8,292,883 B2 | 10/2012 | Kabaya et al. | |
| 8,298,223 B2 | 10/2012 | Wham et al. | |
| 8,303,337 B2 | 11/2012 | Ballard et al. | |
| 8,303,580 B2 | 11/2012 | Wham et al. | |
| 8,333,759 B2 | 12/2012 | Podhajsky | |
| 8,346,370 B2 | 1/2013 | Haley et al. | |
| 8,353,903 B2 | 1/2013 | Podhajsky | |
| 8,353,905 B2 | 1/2013 | Jensen et al. | |
| 8,377,053 B2 | 2/2013 | Orszulak | |
| 8,377,054 B2 | 2/2013 | Gilbert | |
| 8,382,751 B2 | 2/2013 | Gilbert et al. | |
| 8,398,627 B2 | 3/2013 | Hosier | |
| 8,403,924 B2 | 3/2013 | Behnke et al. | |
| 8,409,186 B2 | 4/2013 | Behnke et al. | |
| 8,454,590 B2 | 6/2013 | Smith | |
| 8,460,284 B2 | 6/2013 | Aronow et al. | |
| 8,469,956 B2 | 6/2013 | McKenna et al. | |
| 8,475,447 B2 | 7/2013 | Orszulak et al. | |
| 8,485,993 B2 | 7/2013 | Orszulak et al. | |
| 8,486,061 B2 | 7/2013 | Podhajsky | |
| 8,512,232 B2 | 8/2013 | Rothberg et al. | |
| 8,523,855 B2 | 9/2013 | Keppel | |
| 8,540,709 B2 | 9/2013 | Allen | |
| 8,542,019 B2 | 9/2013 | Brannan et al. | |
| 2002/0022836 A1* | 2/2002 | Goble | A61B 18/042 606/34 |
| 2002/0029036 A1 | 3/2002 | Goble et al. | |
| 2003/0153908 A1 | 8/2003 | Goble et al. | |
| 2003/0181898 A1 | 9/2003 | Bowers | |
| 2003/0229344 A1 | 12/2003 | Dycus et al. | |
| 2004/0015159 A1 | 1/2004 | Slater et al. | |
| 2004/0030330 A1 | 2/2004 | Brassell et al. | |
| 2004/0068304 A1 | 4/2004 | Paton et al. | |
| 2004/0097912 A1 | 5/2004 | Gonnering | |
| 2004/0116919 A1 | 6/2004 | Heim et al. | |
| 2004/0133189 A1 | 7/2004 | Sakurai | |
| 2004/0172016 A1 | 9/2004 | Bek et al. | |
| 2004/0193021 A1 | 9/2004 | Zdeblick et al. | |
| 2005/0004634 A1 | 1/2005 | Ricart et al. | |
| 2005/0021020 A1 | 1/2005 | Blaha | |
| 2005/0109111 A1 | 5/2005 | Manlove et al. | |
| 2005/0109935 A1 | 5/2005 | Manlove et al. | |
| 2005/0131390 A1 | 6/2005 | Heinrich et al. | |
| 2006/0079774 A1 | 4/2006 | Anderson | |
| 2006/0111711 A1 | 5/2006 | Goble | |
| 2006/0155270 A1 | 7/2006 | Hancock et al. | |
| 2006/0161148 A1 | 7/2006 | Behnke | |
| 2006/0191926 A1 | 8/2006 | Ray et al. | |
| 2006/0221452 A1* | 10/2006 | Chen | B60R 1/088 359/603 |
| 2006/0224053 A1 | 10/2006 | Black et al. | |
| 2006/0224152 A1 | 10/2006 | Behnke et al. | |
| 2006/0291178 A1 | 12/2006 | Shih | |
| 2007/0088413 A1 | 4/2007 | Weber et al. | |
| 2007/0093801 A1 | 4/2007 | Behnke | |
| 2007/0173802 A1 | 7/2007 | Keppel | |
| 2007/0173803 A1 | 7/2007 | Wham et al. | |
| 2007/0173805 A1 | 7/2007 | Weinberg et al. | |
| 2007/0173811 A1 | 7/2007 | Couture et al. | |
| 2007/0173813 A1 | 7/2007 | Odom | |
| 2007/0203481 A1 | 8/2007 | Gregg et al. | |
| 2007/0265612 A1 | 11/2007 | Behnke et al. | |
| 2007/0282320 A1 | 12/2007 | Buysse et al. | |
| 2008/0004619 A1 | 1/2008 | Malis et al. | |
| 2008/0015563 A1 | 1/2008 | Hoey et al. | |
| 2008/0015570 A1 | 1/2008 | Ormsby et al. | |
| 2008/0071257 A1 | 3/2008 | Kotmel et al. | |
| 2008/0071260 A1 | 3/2008 | Shores | |
| 2008/0132893 A1 | 6/2008 | D'Amelio et al. | |
| 2008/0147056 A1 | 6/2008 | van der Weide et al. | |
| 2008/0177199 A1 | 7/2008 | Podhajsky | |
| 2008/0203997 A1 | 8/2008 | Foran et al. | |
| 2008/0234574 A1 | 9/2008 | Hancock et al. | |
| 2008/0262489 A1 | 10/2008 | Steinke | |
| 2008/0281311 A1 | 11/2008 | Dunning et al. | |
| 2008/0281315 A1 | 11/2008 | Gines | |
| 2008/0281316 A1 | 11/2008 | Carlton et al. | |
| 2008/0287943 A1 | 11/2008 | Weber et al. | |
| 2008/0319350 A1 | 12/2008 | Wallace et al. | |
| 2009/0018536 A1 | 1/2009 | Behnke | |
| 2009/0030477 A1 | 1/2009 | Jarrard | |
| 2009/0082765 A1 | 3/2009 | Collins et al. | |
| 2009/0146635 A1 | 6/2009 | Qiu et al. | |
| 2009/0157067 A1 | 6/2009 | Kane et al. | |
| 2009/0157071 A1 | 6/2009 | Wham et al. | |
| 2009/0234350 A1 | 9/2009 | Behnke et al. | |
| 2009/0240244 A1 | 9/2009 | Malis et al. | |
| 2009/0248003 A1 | 10/2009 | Orszulak | |
| 2009/0248006 A1 | 10/2009 | Paulus et al. | |
| 2009/0248007 A1 | 10/2009 | Falkenstein et al. | |
| 2009/0254077 A1 | 10/2009 | Craig | |
| 2009/0259224 A1 | 10/2009 | Wham et al. | |
| 2009/0292283 A1 | 11/2009 | Odom | |
| 2010/0030210 A1 | 2/2010 | Paulus | |
| 2010/0042093 A9 | 2/2010 | Wham et al. | |
| 2010/0057076 A1 | 3/2010 | Behnke et al. | |
| 2010/0063494 A1 | 3/2010 | Orszulak | |
| 2010/0063497 A1 | 3/2010 | Orszulak | |
| 2010/0076424 A1 | 3/2010 | Carr | |
| 2010/0082022 A1 | 4/2010 | Haley et al. | |
| 2010/0082023 A1 | 4/2010 | Brannan et al. | |
| 2010/0082083 A1 | 4/2010 | Brannan et al. | |
| 2010/0082084 A1 | 4/2010 | Brannan et al. | |
| 2010/0094271 A1 | 4/2010 | Ward et al. | |
| 2010/0094275 A1 | 4/2010 | Wham | |
| 2010/0094288 A1 | 4/2010 | Kerr | |
| 2010/0114090 A1 | 5/2010 | Hosier | |
| 2010/0168572 A1 | 7/2010 | Sliwa et al. | |
| 2010/0168730 A1 | 7/2010 | Hancock et al. | |
| 2010/0168741 A1 | 7/2010 | Sanai et al. | |
| 2010/0179533 A1 | 7/2010 | Podhajsky | |
| 2010/0191233 A1 | 7/2010 | Wham et al. | |
| 2010/0211063 A1 | 8/2010 | Wham et al. | |
| 2010/0217258 A1 | 8/2010 | Floume et al. | |
| 2010/0217264 A1 | 8/2010 | Odom et al. | |
| 2010/0250209 A1* | 9/2010 | Pearson | A61B 18/1206 703/2 |
| 2010/0268220 A1 | 10/2010 | Johnson et al. | |
| 2010/0318080 A1 | 12/2010 | Keppel | |
| 2011/0028963 A1 | 2/2011 | Gilbert | |
| 2011/0054460 A1 | 3/2011 | Gilbert | |
| 2011/0060329 A1 | 3/2011 | Gilbert et al. | |
| 2011/0071516 A1 | 3/2011 | Gregg | |
| 2011/0071521 A1 | 3/2011 | Gilbert | |
| 2011/0077631 A1 | 3/2011 | Keller | |
| 2011/0077639 A1 | 3/2011 | Brannan et al. | |
| 2011/0087213 A1 | 4/2011 | Messerly et al. | |
| 2011/0112530 A1 | 5/2011 | Keller | |
| 2011/0115562 A1 | 5/2011 | Gilbert | |
| 2011/0140607 A1 | 6/2011 | Moore et al. | |
| 2011/0144635 A1 | 6/2011 | Harper et al. | |
| 2011/0178516 A1 | 7/2011 | Orszulak et al. | |
| 2011/0204903 A1 | 8/2011 | Gilbert | |
| 2011/0208179 A1 | 8/2011 | Prakash et al. | |
| 2011/0213354 A1 | 9/2011 | Smith | |
| 2011/0213355 A1 | 9/2011 | Behnke, II | |
| 2011/0301607 A1 | 12/2011 | Couture | |
| 2011/0318948 A1 | 12/2011 | Plaven et al. | |
| 2011/0319881 A1 | 12/2011 | Johnston | |
| 2012/0004703 A1 | 1/2012 | Deborski et al. | |
| 2012/0010610 A1 | 1/2012 | Keppel | |
| 2012/0022521 A1 | 1/2012 | Odom et al. | |
| 2012/0028373 A1 | 2/2012 | Belen et al. | |

(56) References Cited

U.S. PATENT DOCUMENTS

| | | |
|---|---|---|
| 2012/0029515 A1 | 2/2012 | Couture |
| 2012/0089139 A1 | 4/2012 | Wham et al. |
| 2012/0101491 A1 | 4/2012 | Blaha |
| 2012/0116268 A1 | 5/2012 | Orszulak et al. |
| 2012/0130256 A1 | 5/2012 | Buysse et al. |
| 2012/0150170 A1 | 6/2012 | Buysse et al. |
| 2012/0172866 A1 | 7/2012 | Behnke, II |
| 2012/0179156 A1 | 7/2012 | Behnke, II |
| 2012/0220997 A1 | 8/2012 | Johnston |
| 2012/0239020 A1 | 9/2012 | Cunningham |
| 2012/0239025 A1 | 9/2012 | Smith |
| 2012/0239026 A1 | 9/2012 | Orszulak et al. |
| 2012/0265194 A1 | 10/2012 | Podhajsky |
| 2012/0265195 A1 | 10/2012 | Gilbert |
| 2012/0303017 A1 | 11/2012 | Brannan et al. |
| 2012/0310241 A1 | 12/2012 | Orszulak |
| 2012/0316555 A1 | 12/2012 | Orszulak et al. |
| 2012/0316556 A1 | 12/2012 | Podhajsky |
| 2013/0006235 A1 | 1/2013 | Podhajsky et al. |
| 2013/0023867 A1 | 1/2013 | Collins |
| 2013/0023869 A1 | 1/2013 | Orszulak |
| 2013/0023870 A1 | 1/2013 | Collins |
| 2013/0023871 A1 | 1/2013 | Collins |
| 2013/0035679 A1 | 2/2013 | Orszulak |
| 2013/0041364 A1 | 2/2013 | Orszulak |
| 2013/0041367 A1 | 2/2013 | Wham et al. |
| 2013/0053840 A1 | 2/2013 | Krapohl et al. |
| 2013/0066311 A1 | 3/2013 | Smith et al. |
| 2013/0067725 A1 | 3/2013 | Behnke, II et al. |
| 2013/0072920 A1 | 3/2013 | Behnke, II et al. |
| 2013/0072921 A1 | 3/2013 | Behnke, II et al. |
| 2013/0072922 A1 | 3/2013 | Behnke, II et al. |
| 2013/0072923 A1 | 3/2013 | Behnke, II et al. |
| 2013/0079763 A1 | 3/2013 | Heckel et al. |
| 2013/0158541 A1 | 6/2013 | Orszulak |
| 2013/0178848 A1 | 7/2013 | Gilbert et al. |
| 2013/0184698 A1 | 7/2013 | Behnke, II et al. |
| 2013/0184699 A1 | 7/2013 | Behnke, II et al. |
| 2013/0190750 A1 | 7/2013 | Behnke, II et al. |
| 2013/0190751 A1 | 7/2013 | Brannan |
| 2013/0193952 A1 | 8/2013 | Krapohl |
| 2013/0197510 A1 | 8/2013 | Heckel |
| 2013/0197874 A1 | 8/2013 | Heckel |
| 2013/0249721 A1 | 9/2013 | Smith |
| 2013/0253501 A1 | 9/2013 | Joseph |
| 2013/0261616 A1 | 10/2013 | Prakash et al. |
| 2013/0267944 A1 | 10/2013 | Krapohl |
| 2013/0274729 A1 | 10/2013 | Orszulak |
| 2013/0304049 A1 | 11/2013 | Behnke, II et al. |
| 2013/0345696 A1 | 12/2013 | Behnke, II et al. |
| 2014/0002056 A1 | 1/2014 | Moul et al. |
| 2014/0015535 A1 | 1/2014 | Lopez |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 0309942 A2 | 4/1989 |
| EP | 310431 A2 | 4/1989 |
| EP | 325456 A2 | 7/1989 |
| EP | 336742 A2 | 10/1989 |
| EP | 390937 A1 | 10/1990 |
| EP | 0503200 A2 | 9/1992 |
| EP | 0 556 705 A1 | 8/1993 |
| EP | 569130 A1 | 11/1993 |
| EP | 608609 A2 | 8/1994 |
| EP | 617925 A1 | 10/1994 |
| EP | 694291 A1 | 1/1996 |
| EP | 0 836 868 A2 | 4/1998 |
| EP | 870473 A2 | 10/1998 |
| EP | 0878169 A1 | 11/1998 |
| EP | 880220 A2 | 11/1998 |
| EP | 0 882 955 A1 | 12/1998 |
| EP | 0640317 B1 | 9/1999 |
| EP | 1051948 A2 | 11/2000 |
| EP | 1053720 | 11/2000 |
| EP | 1146827 A1 | 10/2001 |
| EP | 1151725 A1 | 11/2001 |
| EP | 1157667 A2 | 11/2001 |
| EP | 1263181 A1 | 12/2002 |
| EP | 1278007 | 1/2003 |
| EP | 1293171 A2 | 3/2003 |
| EP | 1366724 A1 | 12/2003 |
| EP | 1472984 | 11/2004 |
| EP | 1495712 A1 | 1/2005 |
| EP | 1500378 A1 | 1/2005 |
| EP | 1535581 | 6/2005 |
| EP | 1594392 A2 | 11/2005 |
| EP | 1609430 | 12/2005 |
| EP | 1645235 A1 | 4/2006 |
| EP | 1681026 A2 | 7/2006 |
| EP | 1707143 | 10/2006 |
| EP | 1707144 A1 | 10/2006 |
| EP | 1744354 A2 | 1/2007 |
| EP | 1776929 A1 | 4/2007 |
| EP | 1810628 | 7/2007 |
| EP | 1810630 A1 | 7/2007 |
| EP | 1810631 A2 | 7/2007 |
| EP | 1810632 A1 | 7/2007 |
| EP | 1810633 A1 | 7/2007 |
| EP | 1810634 A1 | 7/2007 |
| EP | 1849425 A1 | 10/2007 |
| EP | 1854423 A2 | 11/2007 |
| EP | 1862137 A1 | 12/2007 |
| EP | 1902681 A1 | 3/2008 |
| EP | 1990905 A2 | 11/2008 |
| EP | 1994904 | 11/2008 |
| EP | 2025297 A2 | 2/2009 |
| EP | 2042116 | 4/2009 |
| EP | 2100566 A1 | 9/2009 |
| EP | 2111812 A2 | 10/2009 |
| EP | 2156800 A1 | 2/2010 |
| EP | 2253286 A1 | 11/2010 |
| EP | 2301463 A1 | 3/2011 |
| EP | 2329782 A1 | 6/2011 |
| EP | 2345454 A1 | 7/2011 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| GB | 607850 A | 9/1948 |
| GB | 702510 A | 1/1954 |
| GB | 855459 A | 11/1960 |

(56) References Cited

FOREIGN PATENT DOCUMENTS

| | | |
|---|---|---|
| GB | 902775 A | 8/1962 |
| GB | 1290304 A | 9/1972 |
| GB | 2154881 A | 9/1985 |
| GB | 2164473 A | 3/1986 |
| GB | 2214430 A | 9/1989 |
| GB | 2331247 A | 5/1999 |
| GB | 2358934 A | 8/2001 |
| GB | 2434872 A | 8/2007 |
| JP | 63 005876 A | 1/1988 |
| JP | 2002-065690 A | 3/2002 |
| JP | 2005-185657 A | 7/2005 |
| SU | 166452 | 11/1964 |
| SU | 727201 A2 | 4/1980 |
| WO | 92/06642 | 4/1992 |
| WO | 92/07622 A1 | 5/1992 |
| WO | 93/20747 A1 | 10/1993 |
| WO | 93/24066 A1 | 12/1993 |
| WO | 94/10922 A1 | 5/1994 |
| WO | 94/24949 A1 | 11/1994 |
| WO | 94/28809 A1 | 12/1994 |
| WO | 95/09577 A1 | 4/1995 |
| WO | 95/18575 A1 | 7/1995 |
| WO | 95/19148 A1 | 7/1995 |
| WO | 95/25471 A2 | 9/1995 |
| WO | 95/25472 A1 | 9/1995 |
| WO | 96/02180 A2 | 2/1996 |
| WO | 96/04860 A1 | 2/1996 |
| WO | 96/08794 A1 | 3/1996 |
| WO | 96/18349 A2 | 6/1996 |
| WO | 96/29946 A1 | 10/1996 |
| WO | 96/39085 A1 | 12/1996 |
| WO | 96/39086 A1 | 12/1996 |
| WO | 96/39088 A1 | 12/1996 |
| WO | 96/39914 A1 | 12/1996 |
| WO | 97/06739 A2 | 2/1997 |
| WO | 97/06740 A2 | 2/1997 |
| WO | 97/06855 A2 | 2/1997 |
| WO | 97/10763 A1 | 3/1997 |
| WO | 97/11648 A2 | 4/1997 |
| WO | 97/17029 A1 | 5/1997 |
| WO | 97/43971 A2 | 11/1997 |
| WO | 98/07378 A1 | 2/1998 |
| WO | 98/18395 A1 | 5/1998 |
| WO | 98/27880 | 7/1998 |
| WO | 99/12607 A1 | 3/1999 |
| WO | 99/56647 A1 | 11/1999 |
| WO | 00/48672 A1 | 8/2000 |
| WO | 00/54683 A1 | 9/2000 |
| WO | 01/01847 | 1/2001 |
| WO | 02/00129 | 1/2002 |
| WO | 02/11634 | 2/2002 |
| WO | 02/32333 | 4/2002 |
| WO | 02/32335 | 4/2002 |
| WO | 02/45589 | 6/2002 |
| WO | 02/47565 | 6/2002 |
| WO | 02/053048 A1 | 7/2002 |
| WO | 02/088128 A1 | 11/2002 |
| WO | 03/047446 A1 | 6/2003 |
| WO | 03/090635 A1 | 11/2003 |
| WO | 03/092520 A1 | 11/2003 |
| WO | 03/090630 A3 | 4/2004 |
| WO | 2004/028385 A1 | 4/2004 |
| WO | 2004/043240 A2 | 5/2004 |
| WO | 2004/047659 A2 | 6/2004 |
| WO | 2004/052182 A2 | 6/2004 |
| WO | 2004/073488 | 9/2004 |
| WO | 2004/098385 A2 | 11/2004 |
| WO | 2004/103156 | 12/2004 |
| WO | 2005/046496 A1 | 5/2005 |
| WO | 2005/048809 | 6/2005 |
| WO | 2005/050151 | 6/2005 |
| WO | 2005/060365 A2 | 7/2005 |
| WO | 2005/060849 A1 | 7/2005 |
| WO | 2005/115235 A1 | 12/2005 |
| WO | 2005/117735 A1 | 12/2005 |
| WO | 2006/050888 A1 | 5/2006 |
| WO | 2006/105121 A2 | 10/2006 |
| WO | 2007/055491 A1 | 5/2007 |
| WO | 2007/067522 A2 | 6/2007 |
| WO | 2007/076924 A2 | 7/2007 |
| WO | 2007/105963 A1 | 9/2007 |
| WO | 2008/002517 A1 | 1/2008 |
| WO | 2008/003058 A2 | 1/2008 |
| WO | 2008/011575 A1 | 1/2008 |
| WO | 2008/043999 A2 | 4/2008 |
| WO | 2008/044000 A1 | 4/2008 |
| WO | 2008/044013 A2 | 4/2008 |
| WO | 2008/053532 A1 | 5/2008 |
| WO | 2008/070562 A1 | 6/2008 |
| WO | 2008/071914 A2 | 6/2008 |
| WO | 2008/101356 A1 | 8/2008 |
| WO | 2008/110756 A2 | 9/2008 |
| WO | 2010/129348 A1 | 11/2010 |

OTHER PUBLICATIONS

European Search Report issued in corresponding EP application No. 14178904.0 on Dec. 9, 2014.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.

(56) References Cited

OTHER PUBLICATIONS

Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha Cn, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System" 2 pp. Nov. 1995.

U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 13/943,518 dated Jul. 16, 2013 inventor: Orszulak et al.
U.S. Appl. No. 14/069,534 dated Nov. 1, 2013 inventor: Digmann.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/183,196 dated Feb. 18, 2014 inventor: Krapohl.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/192,112 dated Feb. 27, 2014 inventor: Weinberg.
U.S. Appl. No. 14/255,051 dated Apr. 17, 2014 inventor: Coulson.

\* cited by examiner

SYSTEMS AND METHODS FOR MEASURING TISSUE IMPEDANCE THROUGH AN ELECTROSURGICAL CABLE

CROSS-REFERENCE TO RELATED APPLICATIONS

The present application claims the benefit of and priority to U.S. Provisional Application Nos. 61/859,601, filed on Jul. 29, 2013, and 61/859,624, filed on Jul. 29, 2013. The present application is related to U.S. patent application Ser. No. 14/180,965, filed on Feb. 14, 2014. The entire contents of the above applications are incorporated herein by reference.

BACKGROUND

1. Technical Field

The present disclosure relates to electrosurgery. More particularly, the present disclosure relates to electrosurgical systems and methods for measuring tissue impedance through an electrosurgical cable.

2. Background of Related Art

Electrosurgery involves the application of high-frequency electric current to cut or modify biological tissue during an electrosurgical procedure. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The alternating current typically has a frequency above 100 kilohertz (kHz) to avoid muscle and/or nerve stimulation.

During electrosurgery, the AC generated by the electrosurgical generator is conducted through tissue disposed between the active and return electrodes. The tissue's impedance converts the electrical energy (also referred to as electrosurgical energy) associated with the AC into heat, which causes the tissue temperature to rise. The electrosurgical generator controls the heating of the tissue by controlling the electric power (i.e., electrical energy per time) provided to the tissue. Although many other variables affect the total heating of the tissue, increased current density usually leads to increased heating. The electrosurgical energy is typically used for cutting, dissecting, ablating, coagulating, and/or sealing tissue.

The two basic types of electrosurgery employed are monopolar and bipolar electrosurgery. Both of these types of electrosurgery use an active electrode and a return electrode. In bipolar electrosurgery, the surgical instrument includes an active electrode and a return electrode on the same instrument or in very close proximity to one another, which cause current to flow through a small amount of tissue. In monopolar electrosurgery, the return electrode is located elsewhere on the patient's body and is typically not a part of the electrosurgical instrument itself. In monopolar electrosurgery, the return electrode is part of a device typically referred to as a return pad.

Electrosurgical generators make use of voltage and current sensors to measure quantities, such as power and tissue impedance, for controlling the output of the electrosurgical generator to achieve a desired clinical effect. The voltage and current sensors are often located inside the electrosurgical generators to save costs associated with incorporating sensors into the surgical instruments. A cable, which may be more than a meter in length, connects the electrosurgical generator to the active and return electrodes and is used to deliver electrosurgical energy to tissue being treated.

The cable creates a circuit network between the voltage and current sensors and the tissue being treated, which results in inaccurate power and impedance measurements. Thus, to more accurately measure power and impedance, many generators employ compensation algorithms that account for the impedance of the cable's circuit network. These compensation algorithms typically involve solving Kirchhoff current and voltage equations for multiple nodes in a circuit model that models the cable's circuit network. However, solutions to these equations, when implemented by a real-time embedded software system, may require a significant amount of memory and processing power.

SUMMARY

The electrosurgical systems and methods of the present disclosure reduce the amount of memory and processing power needed to accurately measure power and tissue impedance by using impedance equations that are based on AC filters.

In one aspect, the present disclosure features an electrosurgical generator that delivers electrosurgical energy to tissue via a cable and an instrument coupled to the cable. The electrosurgical generator includes an output stage that generates electrosurgical energy, a plurality of sensors that sense a voltage waveform and a current waveform of the generated electrosurgical energy, and a controller that controls the output stage to achieve a desired level of the electrosurgical energy. The controller includes a calculator that calculates a real part of an impedance based on the sensed voltage and current waveforms, an estimator that estimates a resistance of the tissue using a solution to a quadratic equation that is a function of a real part of the impedance, and a control signal generator that generates a control signal for controlling the output stage based on the resistance of the tissue.

The estimator may use the calculated real part of the impedance value as the estimate of the resistance of the tissue when the calculated real part of the impedance value is less than a predetermined value.

The solution to the quadratic equation may be $$R_{load} = \frac{1 \pm \sqrt{1 - 4 \cdot (\omega \cdot C_{cable} \cdot \text{Re}(Z))^2}}{2 \cdot \text{Re}(Z) \cdot (\omega \cdot C_{cable})^2},$$

where $R_{load}$ is the resistance of the tissue, $\omega$ is the frequency of the generated electrosurgical energy, $C_{cable}$ is the shunt capacitance of a cable connecting the electrosurgical generator to an electrosurgical instrument, and $\text{Re}(Z)$ is the real part of the impedance.

The quadratic equation may be derived from a model of the cable having a series inductor and a shunt capacitor. The resistance of the tissue may be the solution to the quadratic equation. The larger solution may be used when a phase difference between the voltage waveform and the current waveform is less than or equal to −45 degrees and the smaller solution may be used when the phase difference is greater than −45 degrees.

The electrosurgical generator may include a memory for storing a lookup table that maps a plurality of values of the real part of the impedance to a plurality of corresponding values of the resistances of the tissue that are calculated according to a solution to the quadratic equation that is a function of the real part of the impedance. The estimator may then estimate the resistance of the tissue by accessing the look up table to determine an estimated resistance of the tissue corresponding to the calculated real part of the impedance.

When the calculated real part of the impedance is between two real part of the impedance values in the look up table, the estimator may select the estimated resistance of the tissue corresponding the real part of the impedance value in the look up table that is nearest to the calculated real part of the impedance or may interpolate between the two real part of the impedance values in the look up table to determine the estimated resistance of the tissue.

The estimator may estimate the resistance of the tissue using a polynomial equation that is determined by performing a polynomial curve fit to the solution to the quadratic equation that is a function of the real part of the impedance. The polynomial equation may be a second-order polynomial equation.

The electrosurgical generator may include an inductor coupled to the output stage and tuned to a shunt capacitance and a series inductance of the cable so that the calculated real part of the impedance is sufficiently resistive. The shunt capacitance of the cable may be a capacitance value measured when electrodes of the instrument are not in contact with tissue. The inductance value of the inductor may be equal to $$\frac{1}{\omega^2 C_{cable}} - L_{cable},$$

where $\omega$ is the frequency of the generated electrosurgical energy, $C_{cable}$ is the shunt capacitance of a cable connecting the electrosurgical generator to an electrosurgical instrument, and $L_{cable}$ is the series inductance of the cable.

In still another aspect, the present disclosure features a method of controlling an electrosurgical generator that delivers electrosurgical energy to tissue via a cable and an instrument coupled to the cable. The method includes sensing a voltage waveform and a current waveform of the generated electrosurgical energy, calculating a real part of an impedance based on the sensed voltage and current waveforms, estimating a resistance of the tissue using a solution to a quadratic equation that is a function of a real part of the impedance, and generating a control signal for an output stage of the electrosurgical generator based on the resistance of the tissue.

The method may include determining whether the calculated real part of the impedance value is less than a predetermined value and using the calculated real part of the impedance value as the estimate of the resistance of the tissue when the calculated real part of the impedance value is less than the predetermined value.

The solution to the quadratic equation may be $$R_{load} = \frac{1 \pm \sqrt{1 - 4 \cdot (\omega \cdot C_{cable} \cdot Re(Z))^2}}{2 \cdot Re(Z) \cdot (\omega \cdot C_{cable})^2},$$

where $R_{load}$ is the resistance of the tissue, $\omega$ is the frequency of the generated electrosurgical energy, $C_{cable}$ is the shunt capacitance of a cable connecting the electrosurgical generator to an electrosurgical instrument, and $Re(Z)$ is the real part of the impedance.

The quadratic equation may be derived from a model of the cable having a series inductor and a shunt capacitor. The method may include using the larger solution to the quadratic equation as the estimate of the resistance of the tissue when a phase difference between the voltage waveform and the current waveform is less than or equal to −45 degrees, or using the smaller solution to the quadratic equation as the estimate of the resistance of the tissue when the phase difference is greater than −45 degrees.

The method may include storing a lookup table that maps a plurality of values of the real part of the impedance to a plurality of corresponding values of the resistances of the tissue that are calculated according to a solution to the quadratic equation that is a function of the real part of the impedance, and estimating the resistance of the tissue by accessing the look up table to determine an estimated resistance of the tissue corresponding to the calculated real part of the impedance.

When the calculated real part of the impedance is between two real part of the impedance values in the look up table, estimating the resistance of the tissue may include selecting the estimated resistance of the tissue corresponding the real part of the impedance value in the look up table that is nearest to the calculated real part of the impedance or interpolating between the two real part of the impedance values in the look up table to determine the estimated resistance of the tissue.

Estimating the resistance of the tissue may include using a polynomial equation that is determined by performing a polynomial curve fit to the solution to the quadratic equation that is a function of the real part of the impedance. The polynomial equation may be a second-order polynomial equation.

BRIEF DESCRIPTION OF THE DRAWINGS

Various embodiments of the present disclosure are described with reference to the accompanying drawings wherein.

DETAILED DESCRIPTION

As described above, the cable in an electrosurgical system creates a circuit network between the voltage and current sensors and the tissue being treated, which results in inaccurate power and impedance measurements. Thus, to more accurately measure power and impedance, many generators employ compensation algorithms that account for the impedance of the cable's circuit network. These compensation algorithms involve the measurement and storage of multiple cable parameters, such as series inductance, shunt capacitance, and resistance, which are used as constants in the solutions to the Kirchhoff current and voltage equations for multiple nodes in the model of the cable's circuit network. The compensation algorithms also involve many mathematical operations, e.g., multiplies and additions, on complex numbers having real and imaginary components.

The electrosurgical systems and methods of the present disclosure reduce the amount of memory and processing power needed to accurately measure tissue impedance. The systems and methods according to the present disclosure employ a simple model of the cable for estimating the actual tissue impedance. The cable model includes an inductor and a resistance in series with the tissue being treated, and a shunt capacitor in parallel with the tissue being treated. The resistance of the cable 715 (shown in FIG. 7) is relatively small compared to the resistance of the tissue being treated and thus may be ignored. Based on sensed current and voltage waveforms, a real part of the impedance is calculated and the actual tissue impedance is estimated based on the calculated real part of the impedance.

As disclosed in U.S. Patent Application No. 61/794,191, which is incorporated by reference in its entirety, the real part of the impedance may be obtained by determining a complex-valued voltage and a complex-valued current using narrowband filters, and calculating a real part of an impedance of the tissue using the complex-valued voltage and the complex-valued current. The real part of the tissue impedance may be calculated according to the following equation:

$$\frac{ac+bd}{c^2+d^2},$$

where a is the real part of the complex-valued voltage, b is the imaginary part of the complex-valued voltage, c is the real part of the complex-valued current, and d is the imaginary part of the complex-valued current. The narrowband filters may be polyphase decimator filters or Goertzel DFT filters. The polyphase decimator filters may be heterodyned carrier-centered polyphase filters having a center frequency that is a harmonic multiple of a frequency of the electrosurgical energy.

Figure 1:
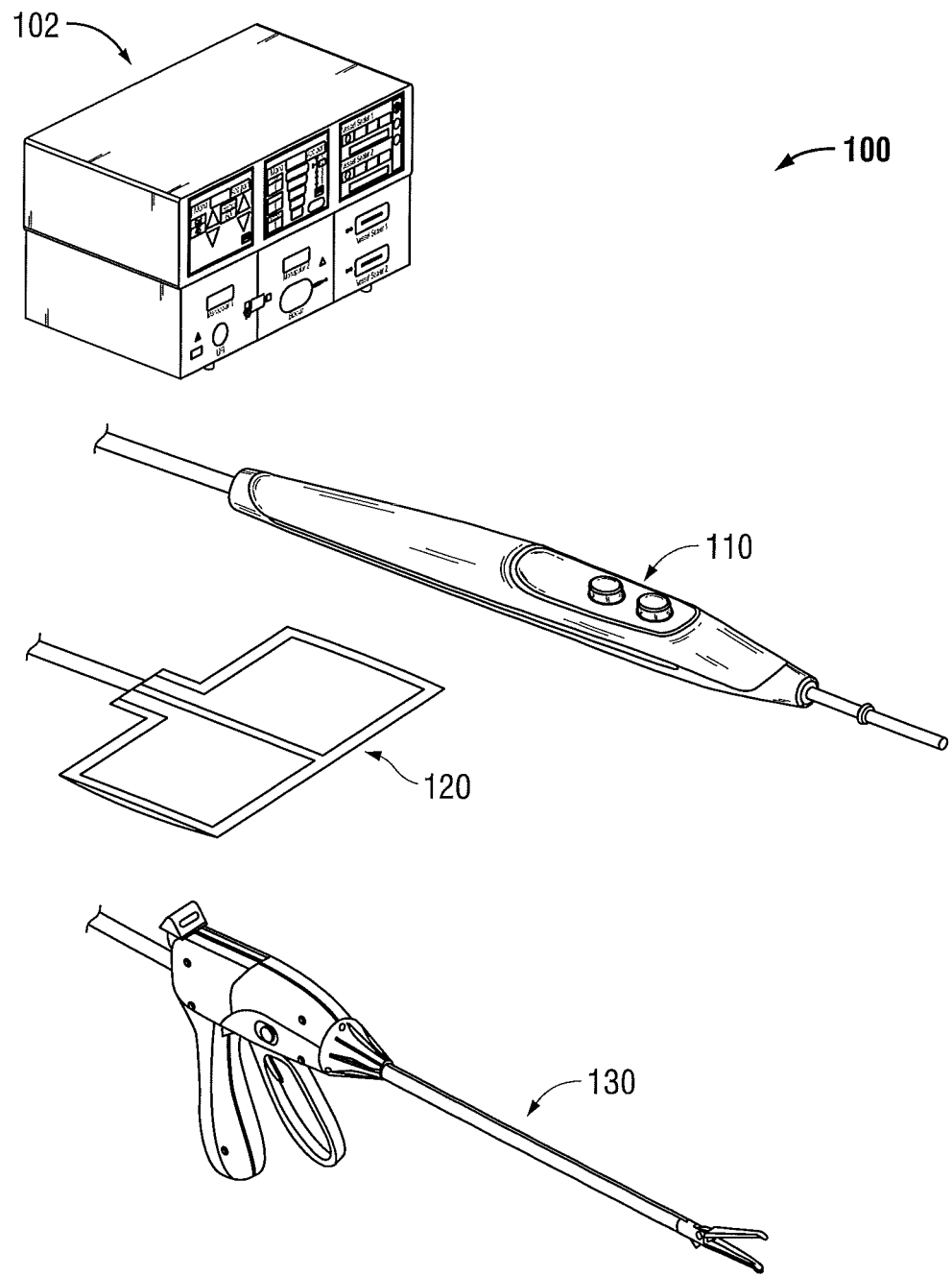
FIG. 1 is an electrosurgical system in accordance with embodiments of the present disclosure.

FIG. 1 illustrates an electrosurgical system 100 in accordance with embodiments of the present disclosure. The electrosurgical system 100 includes an electrosurgical generator 102 which generates electrosurgical energy to treat tissue of a patient. The electrosurgical generator 102 generates an appropriate level of electrosurgical energy based on the selected mode of operation (e.g., cutting, coagulating, ablating, or sealing) and/or the sensed voltage and current waveforms of the generated electrosurgical energy. The electrosurgical system 100 may also include a plurality of output connectors corresponding to a variety of electrosurgical instruments.

The electrosurgical system 100 further includes a monopolar electrosurgical instrument 110 having an electrode for treating tissue of the patient (e.g., an electrosurgical cutting probe or ablation electrode) with a return pad 120. The monopolar electrosurgical instrument 110 can be connected to the electrosurgical generator 102 via one of the plurality of output connectors. The electrosurgical generator 102 may generate electro surgical energy in the form of radio frequency (RF) energy. The electrosurgical energy is supplied to the monopolar electrosurgical instrument 110, which applies the electrosurgical energy to tissue. The electrosurgical energy is returned to the electrosurgical generator 102 through the return pad 120. The return pad 120 provides sufficient contact area with the patient's tissue so as to minimize the risk of tissue damage due to the electrosurgical energy applied to the tissue.

The electrosurgical system 100 also includes a bipolar electrosurgical instrument 130. The bipolar electrosurgical instrument 130 can be connected to the electrosurgical generator 102 via one of the plurality of output connectors. The electrosurgical energy is supplied to one of the two forceps, is applied to tissue, and is returned to the electrosurgical generator 102 through the other forceps.

The electrosurgical generator 102 may be any suitable type of generator and may include a plurality of connectors to accommodate various types of electrosurgical instruments (e.g., monopolar electrosurgical instrument 110 and bipolar electrosurgical instrument 130). The electro surgical generator 102 may also be configured to operate in a variety of modes, such as ablation, cutting, coagulation, and sealing. The electrosurgical generator 102 may include a switching mechanism (e.g., relays) to switch the supply of RF energy among the connectors to which various electrosurgical instruments may be connected. For example, when a monopolar electrosurgical instrument 110 is connected to the electrosurgical generator 102, the switching mechanism switches the supply of RF energy to the monopolar plug. In embodiments, the electrosurgical generator 102 may be configured to provide RF energy to a plurality instruments simultaneously.

The electro surgical generator 102 includes a user interface having suitable user controls (e.g., buttons, activators, switches, or touch screens) for providing control parameters to the electrosurgical generator 102. These controls allow the user to adjust parameters of the electrosurgical energy (e.g., the power level or the shape of the output waveform) so that the electrosurgical energy is suitable for a particular surgical procedure (e.g., coagulating, ablating, tissue sealing, or cutting). The electrosurgical instruments 110 and 130 may also include a plurality of user controls. In addition, the electrosurgical generator 102 may include one or more display screens for displaying a variety of information related to the operation of the electrosurgical generator 102 (e.g., intensity settings and treatment complete indicators).

Figure 2:
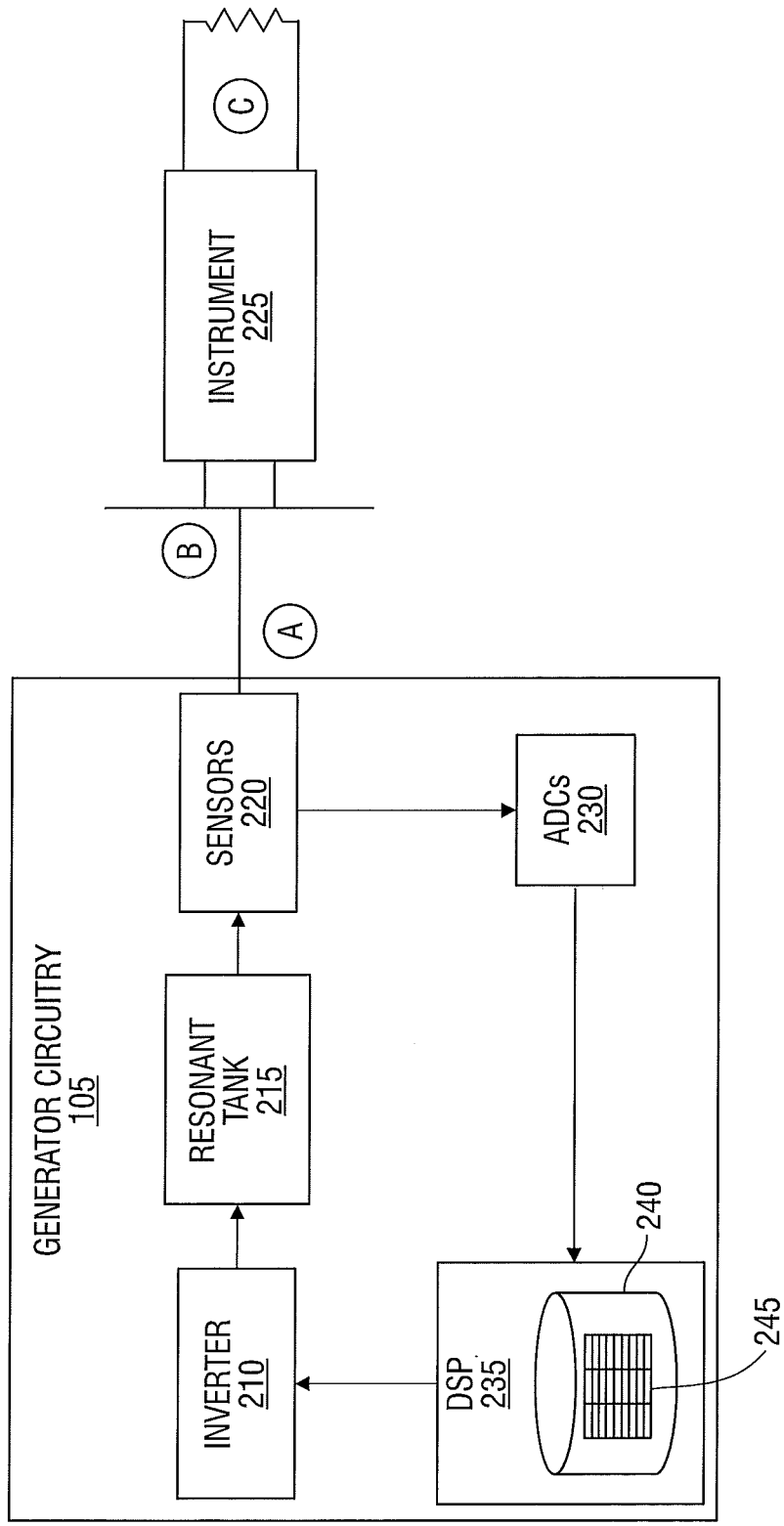
FIG. 2 is a circuit block diagram of the electrosurgical system of FIG. 1.

FIG. 2 is a block diagram of the electrosurgical system 100 of FIG. 1. The electrosurgical system includes generator circuitry 105, which is included in the electrosurgical generator 102 of FIG. 1, and an electrosurgical instrument 225. The generator circuitry 105 includes an inverter 210, a resonant tank circuit 215, a plurality of sensors 220, a plurality of analog-to-digital converters (ADCs) 230, and a digital signal processor 235. The generator circuitry 105 is configured to connect to an alternating current (AC) power source, such as a power outlet, which generates AC having a low frequency (e.g., 25 Hz, 50 Hz, or 60 Hz). The AC power source provides AC power to the generator circuitry 105, which converts the low frequency AC to higher frequency AC that is suitable for a desired electrosurgical procedure. Specifically, the inverter 210 inverts the DC to AC. The AC waveform has a frequency suitable for an electrosurgical procedure (e.g., 472 kHz, 29.5 kHz, and 19.7 kHz).

The appropriate frequency for the electrosurgical energy may differ based on the electrosurgical procedures and modes of electrosurgery. For example, nerve and muscle stimulations cease at about 100,000 cycles per second (100 kHz) and some electrosurgical procedures can be performed safely at a radio frequency (RF) above 100 kHz. At frequencies over 100 kHz, the electrosurgical energy can pass through a patient to targeted tissue with minimal neuromuscular stimulation. For example, ablation uses a frequency of 472 kHz. Other electrosurgical procedures can be performed at frequencies lower than 100 kHz, e.g., 29.5 kHz or 19.7 kHz, with minimal risk of damaging nerves and muscles. The inverter 210 can output AC signals with various frequencies suitable for electrosurgical operations.

The resonant tank circuit 215 is coupled to the inverter 210. The resonant tank circuit 215 matches the impedance at inverter 210 to the impedance of the tissue so that there is maximum or optimal power transfer from the inverter 210 to the tissue being treated. The plurality of sensors 220 are coupled to the resonant tank circuit 215 and the electrosurgical instrument 225 to sense the voltage and current output from the generator circuitry 105 to the electrosurgical instrument 225. Point (A) indicates the impedance as seen from the perspective of the generator circuitry 105. In other words, the generator circuitry 105 sees the impedance of the electrosurgical instrument 225 and the tissue being treated together at point (A). The generator circuitry 105 is configured to compensate for the impedance in the cable disposed between points (A) and (B) so that the generator circuitry 105 can determine the actual impedance of the tissue at point (C).

The plurality of sensors 220 may include two or more pairs or sets of voltage and current sensors that provide redundant measurements of the voltage and current waveforms. This redundancy ensures the reliability, accuracy, and stability of the voltage and current measurements at the output of the inverter 210. In embodiments, the plurality of sensors 220 may include fewer or more sets of voltage and current sensors depending on the application or the design requirements.

The sensed voltage and current waveforms are digitally sampled by the plurality of ADCs 230 to obtain digital samples of the voltage and current waveforms sensed by the sensors 220. The plurality of ADCs 230 may sample the sensed voltage and current waveforms at a frequency that is an integer multiple of the frequency of the voltage and current generated by the electrosurgical generator 102. The sampled current and voltage waveforms are provided to the DSP 235, which includes a calculator for calculating the real part of the impedance of the tissue being treated using the sampled current and voltage waveforms, and an estimator for estimating the resistance of the tissue being treated based on the calculated real part of the tissue impedance. The DSP 235 further includes a control signal generator that generates control signals to control the output voltage and current waveforms of the inverter 210 based on the estimated resistance of the tissue. The DSP 235 includes a storage device 240 that stores instructions to implement functions for controlling the inverter 210 and information including lookup tables 245 which are used to estimate the actual impedance value of the tissue according to embodiments of the present disclosure.

Figure 3:
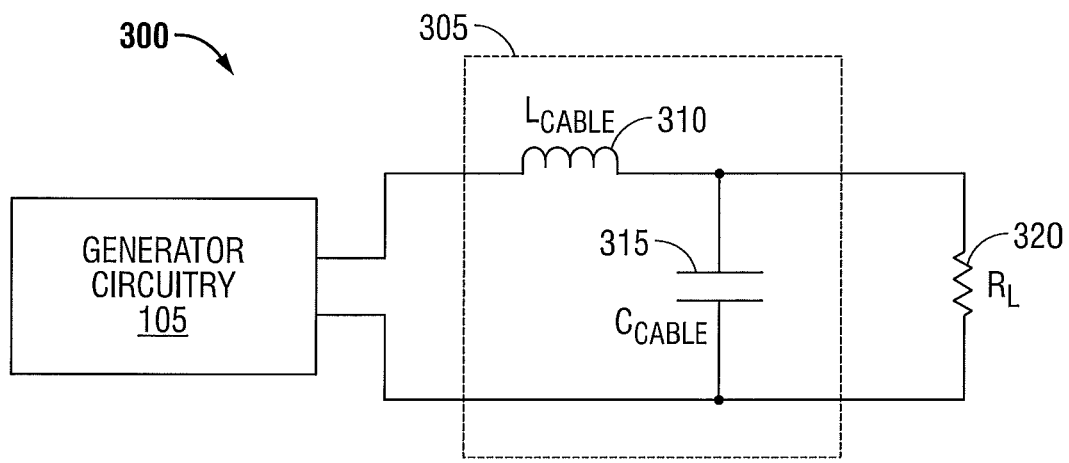
FIG. 3 is a simplified circuit block diagram of the electrosurgical system of FIG. 1 including a model of an electrosurgical cable.

FIG. 3 is a simplified circuit block diagram illustrating an electrosurgical system 300 that includes a cable 305, which is coupled between the generator circuitry 105 and the tissue load 320. As described above, the generator circuitry 105 delivers electrosurgical energy to the tissue 320 via the cable 305. The cable 305 may be modeled as a series inductor $L_{cable}$ 310 coupled to a shunt capacitor $C_{cable}$ 315. The model may also include a series resistance, but because the resistive component is relatively small compared to the resistance of the tissue being treated, the model does not need to include the series resistance.

According to the present disclosure, the generator circuitry 105 determines the actual impedance of the load $R_L$ 320 by compensating for the reactances, i.e., the series inductance Lame 310 and the shunt capacitance $C_{cable}$ 315, of the cable 305. As described in FIG. 2, the impedance seen at point (A) is a combination of total impedance of the cable 305 and the load 320. Theoretically, the total impedance is given by:

$$Z_{total} = \frac{V_m}{I_m} e^{-j\varphi}, \qquad (1)$$

where $Z_{total}$ is the total impedance, $V_m$ is a measured voltage at the sensors 220, $I_m$ is a measured current at the sensors 220, and $\phi$ is the phase difference between the measured voltage and measured current. The phase difference $\phi$ is caused by the reactive components, i.e., the inductance 310 and the capacitance 315, of the cable 305.

Cable compensation is a process of determining the actual resistance $R_L$ of the load 320. Based on the cable model illustrated in FIG. 3, the total impedance is calculated as follows:

$$Z_{total} = j\omega L_C + \left(\frac{1}{j\omega C_C} // R_L\right) = j\omega L_C + \frac{R_L}{j\omega R_L C_C + 1}, \qquad (2)$$

where $\omega$ is the frequency of the voltage and current. Because the total impedance is a complex value, the total impedance has a real part and an imaginary part as follows:

$$Z_{total} = \qquad (3)$$
$$\text{Re}(Z_{total}) + j\text{Im}(Z_{total}) = \frac{R_L}{1+(\omega R_L C_C)^2} + j\left(\omega L_C - \frac{\omega R_L^2 C_C}{1+(\omega R_L C_C)^2}\right).$$

As used herein, the total impedance $Z_{total}$ is also referred to as the impedance Z. Thus, the relationship between the calculated real part of the impedance is:

$$\text{Re}(Z) = \frac{R_L}{1+(\omega R_L C_C)^2}. \qquad (4)$$

Equation (4) can be expressed as a second order polynomial or a quadratic equation with respect to the resistance $R_L$ of the load 320, as follows:

$$(\omega^2 C_C^2 \text{Re}(Z))R_L^2 - R_L + \text{Re}(Z) = 0. \qquad (5)$$

Equation (5) can be solved for the resistance $R_L$ of the load 320 as follows:

$$R_L = \frac{1 \pm \sqrt{1 - 4(\omega C_C \text{Re}(Z))^2}}{2\text{Re}(Z)(\omega C_C)^2}. \tag{6}$$

Based on equation (6), the actual impedance value of the load 320 can be estimated using the calculated real part of the impedance Re(Z), the predetermined capacitance of the cable $C_{cable}$, and the frequency of the electrosurgical energy generated by the generator circuitry 105. The larger solution to equation (6) may be used as the estimate of the tissue resistance when a phase difference between the voltage waveform and the current waveform of the electrosurgical energy is smaller than or equal to −45 degrees and the smaller solution to equation (6) may be used as the estimate of the tissue resistance when the phase difference is greater than −45 degrees.

Figure 4:
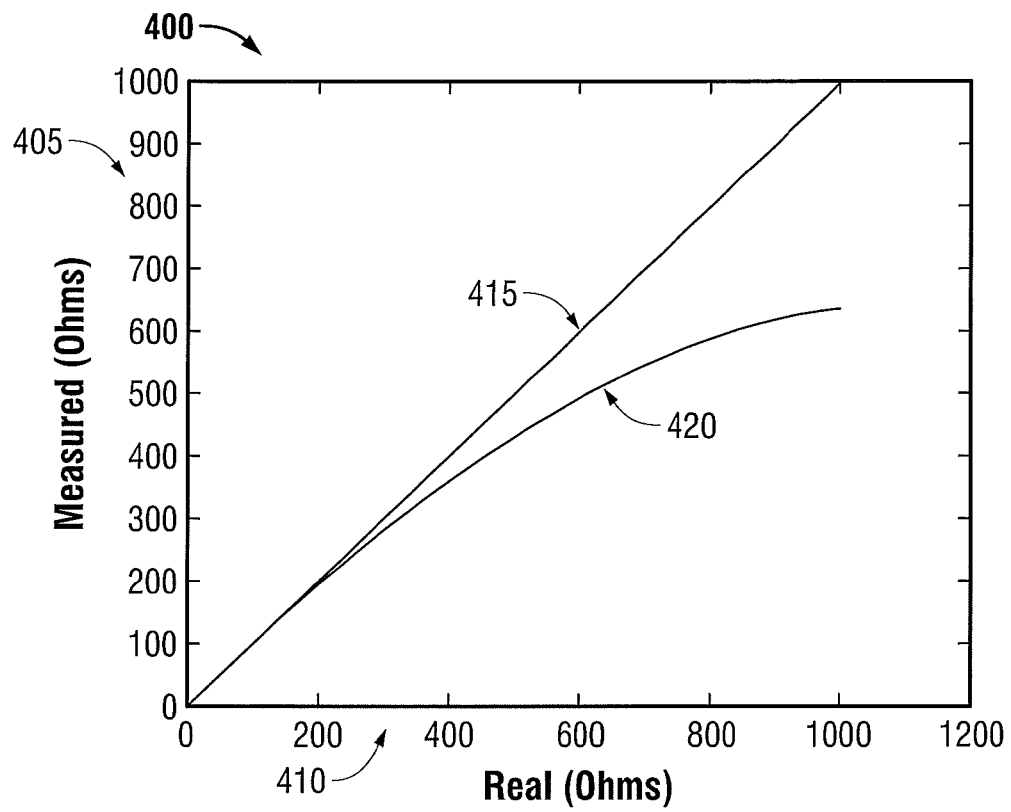
FIG. 4 is a graphical diagram of the real impedance of the tissue and the real part of the impedance measured at the sensors of the electrosurgical generator of FIG. 2.

FIG. 4 is a graphical diagram 400 illustrating how the real part of the impedance as sensed by the generator circuitry 105 is related to the actual real part of the impedance at the load 320, i.e., the resistance of the tissue. The y-axis 405 of graph 400 represents the real part of the impedance Re(Z) in Ohms as measured at the sensors 220 of the generator circuitry 105 of FIG. 2. The x-axis 410 of graph 400 represents the resistance $R_L$ of the load 320 of FIG. 3 in Ohms Ideally, the relationship between the real part of the impedance as measured by the generator circuitry 105 and the real load is a linear relationship as shown by curve 415. Curve 420 is the real part of the impedance Re(Z) that is calculated based on measurements by the sensors 220 of the generator circuitry 105. As shown, curve 420 deviates from the ideal curve 415 as the real impedance increases. However, the two curves 415 and 420 are similar until about 250 Ohms. Thus, the generator circuitry 105 may use the measured real part of the impedance as a measurement of the real load $R_L$ when the real part of the impedance is less than or equal to 250 Ohms or another predetermined resistance. Above 250 Ohms or another predetermined resistance, the generator circuitry 105 may utilize equation (6) to estimate the real load $R_L$ based on the calculated real part of the impedance Re(Z).

According to one method of the present disclosure, the DSP 235 (FIG. 2) calculates the real part of the impedance and estimates the actual real load, e.g., the tissue resistance, according to equation (6) for every measurement cycle. The DSP 235 then generates a control signal to control the inverter 210 based on the estimate of the actual real load. One of the advantages of this method is that it provides an exact solution for every measurement.

According to another method, the DSP 235 pre-populates a lookup table 245 in the DSP's storage device 240 with corrected values or correction factors. The DSP 235, e.g., a software estimator module running on the DSP 235, may then estimate the actual real load values by mapping the real part of the impedance as measured by the sensors 220 of the generator circuitry 105 to the actual real load values. When the calculated real part of the impedance is between two real part of the impedance values in the look up table, the DSP 235 selects the estimated resistance of the tissue corresponding the real part of the impedance value in the look up table that is nearest to the real part of the impedance or interpolates between the two real part of the impedance values in the look up table to determine the estimated resistance of the tissue. While the look-up table method is computationally efficient, it uses more storage and may be less accurate than the method that involves calculating the actual real load according to equation (6).

According to still another method, the DSP 235 corrects or pre-warps the target impedance curve using equation (6) and generates a control signal to control the inverter 210 of the generator circuitry 105 so that the real part of the impedance as measured by the sensors 220 tracks the corrected target impedance curve, which may be stored in a look-up table, e.g., look-up table 245. This pre-warping method is illustrated in the graphical diagram of FIG. 5, in which the y-axis represents the measured real impedance 505 at the sensors 220 and the x-axis represents the real load at the end of the cable 510. Curve 520 is the real load at the end of the cable that is achieved when the DSP 235 controls the output from the generator circuitry 105 to track the target real impedance curve 515. Like the look-up table method for estimating the real load, the pre-warping method is computationally efficient. As compared to the method for estimating the real load by calculating equation (6) every measurement cycle, the pre-warping method uses more storage and is less accurate because, like the look-up table method, the pre-warping method may require interpolation.

According to still another method, a polynomial is fit to a correction factor curve and the correction for the next target Z for each measurement is calculated using the polynomial. For example, if the center frequency is $f_c$=400 kHz and the shunt capacitance of the cable $C_{cable}$ is 330 pF, then the corrected target impedance $Z_{corrected}$ could be calculated from the following second-order polynomial equation:

$$Z_{corrected} = (0.0013 \ast Z \ast Z) + (0.5221 \ast Z) + 26.45, \tag{7}$$

where Z is the target impedance and coefficients of the second order polynomial equation for the corrected target impedance $Z_{corrected}$ are a function of the center frequency $f_c$ and the shunt capacitance of the cable. In some embodiments, the corrected target impedance may be calculated according to a higher-order polynomial equation if more accuracy is needed. The advantage of the polynomial fit method is that it is more computationally efficient than continually evaluating equation (6) above.

Figure 5:
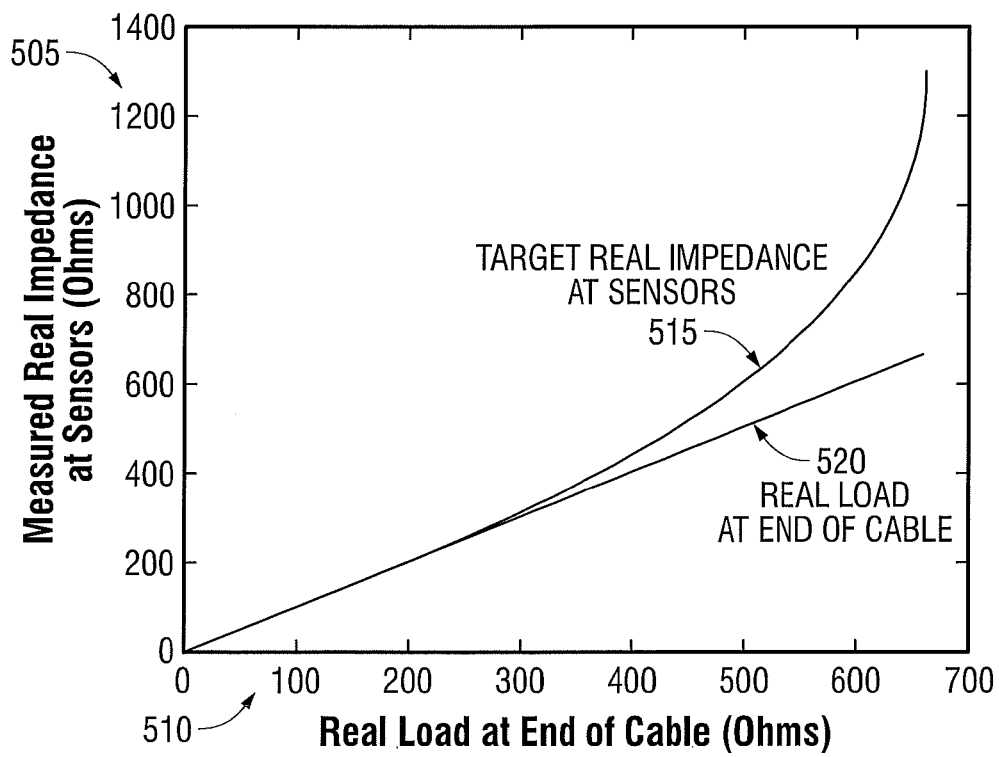
FIG. 5 is a graphical diagram of the ideal impedance of the tissue and the target impedance measured at the sensors of the electrosurgical generator of FIG. 2 according to another embodiment of the present disclosure.
Figure 6:
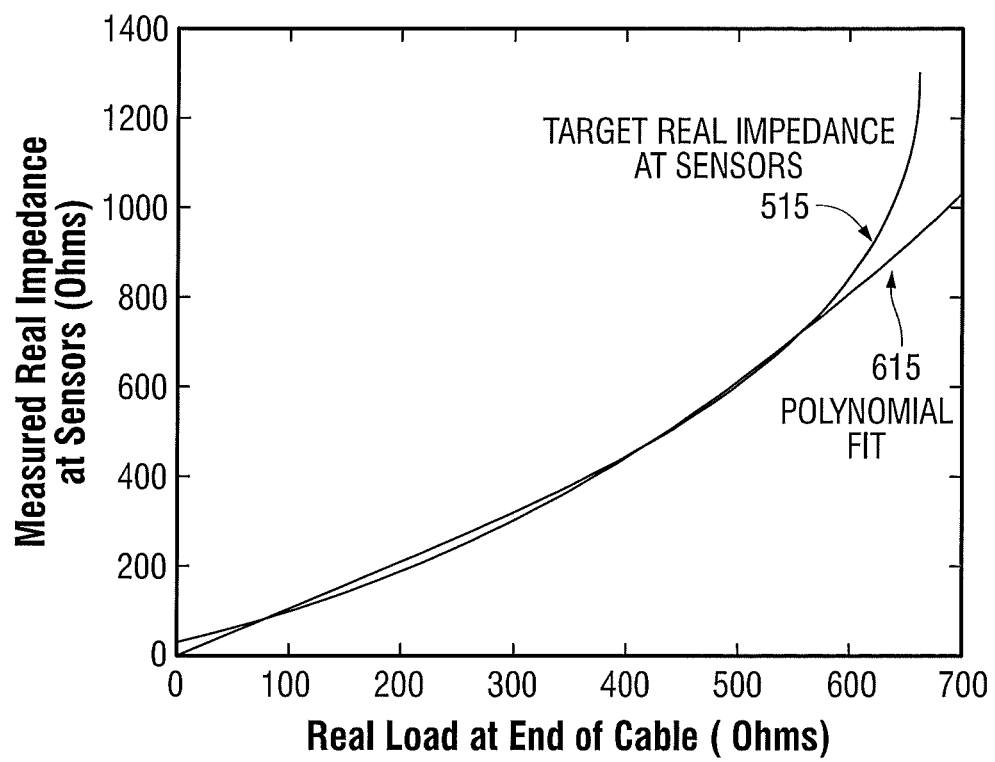
FIG. 6 is a graphical diagram of the ideal target real impedance at the sensors and the polynomial fit to the target real impedance at the sensors of the electrosurgical generator of FIG. 2 according to another embodiment of the present disclosure.

A polynomial may also be fit to the target real impedance curve 515 of FIG. 5. As shown in FIG. 6, curve 615 is a second-order polynomial fit to the target real impedance curve 515. During operation, the DSP 235 controls the inverter 210 of the generator circuitry 105 so that the real part of the impedance measured by the generator circuitry 105 tracks the polynomial fit to the target real impedance curve 615.

Figure 7:
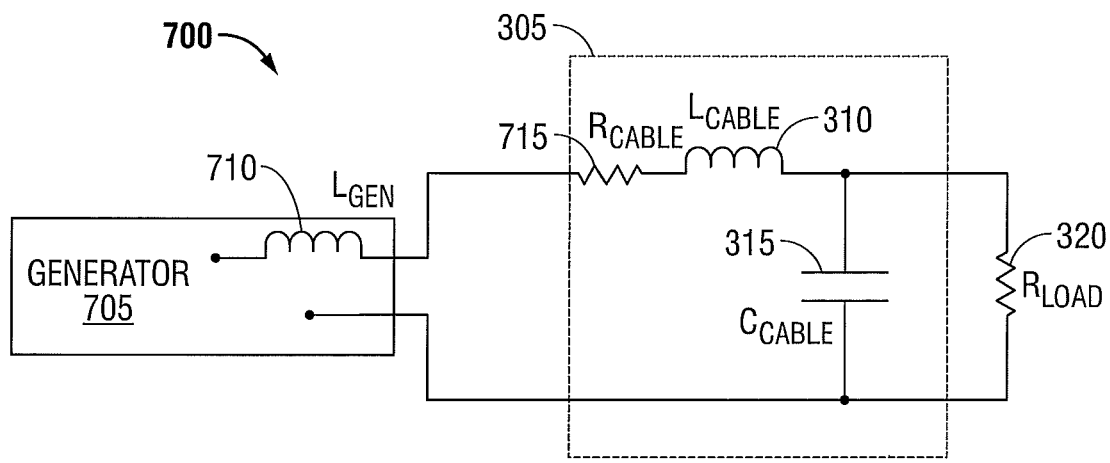
FIG. 7 is a simplified circuit block diagram of the electrosurgical system of FIG. 1, which includes a separate inductor according to another embodiment of the present disclosure.

FIG. 7 shows a circuit block diagram of an electrosurgical system 700 that illustrates a hardware method of compensating for the cable capacitance $C_{cable}$ (315). This is achieved by adding a series inductor 710 having inductance $L_{gen}$ to the generator 705 so that:

$$L_{gen} = -\frac{1}{\omega}\text{Imag}\left\{R_{load} \mathbin{/\mkern-6mu/} \frac{1}{j\omega C_{cable}}\right\} - L_{cable}, \tag{8}$$

where // means "in parallel with," ω is the angular frequency of the generated electrosurgical energy, $R_{load}$ is the resistance of the load 320, $C_{cable}$ is the shunt capacitance 315 of the cable 305 connected to the electrosurgical generator 705, and $L_{cable}$ is the series inductance 310 of the cable 305. After combining the resistance of the load $R_{load}$ with the impedance of the cable capacitance $$\frac{1}{j\omega C_{cable}}$$

in parallel, equation (8) becomes:

$$L_{gen} = -\frac{1}{\omega}\text{Imag}\left\{\frac{R_{load}}{j\omega R_{load} C_{cable} + 1}\right\} - L_{cable}. \quad (9)$$

The series inductor 710 may be connected in series between the sensors 220 and the cable extending between point Ⓐ and point Ⓑ of FIG. 2 (e.g., near point Ⓐ) outside or inside the generator circuitry 105.

Equation (9) may be rewritten to separate out the real and imaginary parts of the parallel combination of the load resistance $R_{load}$ and the impedance of the cable capacitance $$\frac{1}{j\omega C_{cable}}$$

as follows:

$$L_{gen} = -\frac{1}{\omega}\text{Imag}\left\{\frac{R_{load} - j\omega R_{load}^2 C_{cable}}{1 + \omega^2 R_{load}^2 C_{cable}^2}\right\} - L_{cable}. \quad (10)$$

After taking the imaginary part of the parallel combination, equation (10) becomes:

$$L_{gen} = \frac{R_{load}^2 C_{cable}}{1 + \omega^2 R_{load}^2 C_{cable}^2} - L_{cable}, \quad (11)$$

Equation (11) for the inductance $L_{gen}$ can also be expressed as shown below by dividing the numerator and the denominator of the first term by $R_{load}^2$:

$$L_{gen} = \frac{C_{cable}}{\frac{1}{R_{load}^2} + \omega^2 C_{cable}^2} - L_{cable}. \quad (11\text{-a})$$

Here, $$\frac{1}{R_{load}^2}$$

is much smaller than $\omega^2 C_{cable}^2$ and thus is negligible. The inductance $L_{gen}$ may then be expressed as follows:

$$L_{gen} \cong \frac{C_{cable}}{\omega^2 C_{cable}^2} - L_{cable} = \frac{1}{\omega^2 C_{cable}} - L_{cable}, \quad (11\text{-b})$$

As shown, equation (11-b) for the inductance $L_{gen}$ is independent of the resistance of the load $R_{load}$ (i.e., the resistance of the tissue). Thus, the cable capacitance $C_{cable}$(315) may be compensated for by adding a series inductor 710 having inductance $L_{gen}$ determined according to equation (11-b) to the generator 705.

Thus, the total impedance $Z_{total}$ as seen by the sensors 220 (see FIG. 2) at the generator 705 becomes:

$$Z_{total} = j\omega(L_{gen} + L_{cable}) + R_{cable} + R_{load} // \frac{1}{j\omega C_{cable}}. \quad (12)$$

Substituting equation (8) for the series inductance $L_{gen}$ of equation (12) results in the following equation:

$$Z_{total} = j\omega\left\{-\frac{1}{\omega}\text{Imag}\left\{R_{load} // \frac{1}{j\omega C_{cable}}\right\} - L_{cable} + L_{cable}\right\} + \quad (13)$$
$$R_{cable} + \text{Re}\left\{R_{load} // \frac{1}{j\omega C_{cable}}\right\} + j\text{Imag}\left\{R_{load} // \frac{1}{j\omega C_{cable}}\right\}.$$

Since the inductance of the cable $L_{cable}$ is subtracted out of equation (13), equation (13) may be rewritten as follows:

$$Z_{total} = -j\text{Imag}\left\{R_{load} // \frac{1}{j\omega C_{cable}}\right\} + R_{cable} + \quad (14)$$
$$\text{Re}\left\{R_{load} // \frac{1}{j\omega C_{cable}}\right\} + j\text{Imag}\left\{R_{load} // \frac{1}{j\omega C_{cable}}\right\}.$$

Further, as shown in equation (14), the imaginary part of the parallel combination is subtracted out. Thus, equation (14) becomes:

$$Z_{total} = R_{cable} + \text{Re}\left\{R_{load} // \frac{1}{j\omega C_{cable}}\right\}. \quad (15)$$

After combining the resistance of the load $R_{load}$ with the impedance of the cable capacitance $$\frac{1}{j\omega C_{cable}}$$

in parallel, equation (15) becomes:

$$Z_{total} = R_{cable} + \text{Re}\left\{\frac{R_{load}}{j\omega R_{load} C_{cable} + 1}\right\}. \quad (16)$$

Equation (16) may be rewritten to separate out the real and imaginary parts of the parallel combination of the load resistance $R_{load}$ and the impedance of the cable capacitance $$\frac{1}{j\omega C_{cable}}$$

as follows:

$$Z_{total} = R_{cable} + \text{Re}\left\{\frac{R_{load} - j\omega R_{load}^2 C_{cable}}{1 + \omega^2 R_{load}^2 C_{cable}^2}\right\}. \quad (17)$$

After taking the real part of the parallel combination, equation (17) becomes:

$$Z_{total} = R_{cable} + \frac{R_{load}}{1 + \omega^2 R_{load}^2 C_{cable}^2}. \quad (18)$$

Equation (18) indicates that if the inductance $L_{gen}$ of the series inductor 710 is tuned properly, the load presented to the generator circuitry 105 is purely resistive. The advantage of hardware compensation is that software compensation would not be needed if the inductance $L_{gen}$ is properly tuned. Even if the inductance $L_{gen}$ is not properly tuned, the added series inductor 710 would reduce the effects of the shunt capacitance in the cable. The software compensation methods described above may be used in combination with the series inductor 710 to further reduce the effects of the shunt capacitance in the cable. For hardware compensation, the series inductor 710 would need to be tuned for each of the different cables that are used. The series inductor 710 may be placed after the sensors and in series with the cable and the load. The series inductor 710 may alternatively be placed next to the output of the electrosurgical generator.

The cable capacitance C can be determined by turning on the generator with the jaws of the instrument open, that is, setting the real load to, essentially, infinity. Then, the open circuit version of FIG. 3 reduces to:

$$|Z| = \omega C \quad (19)$$

Thus, when |Z| is measured at the sensors 220 of the generator circuitry 105, the capacitance C can be determined.

The systems and methods of measuring tissue impedance described above may be employed in a variety of tissue treatment algorithms including a tissue treatment algorithm having a pre-heating phase and an impedance control phase. At the start of the pre-heating phase, the level of current generated by the generator and supplied to the tissue is low and the impedance of the tissue starts at an initial impedance value. During the pre-heating phase, the level of current supplied to the tissue is increased or ramped upward at a predetermined rate so that the temperature of the tissue increases and the tissue impedance decreases. The ramping of the current continues until (1) the maximum allowable current value is reached, or (2) there is a "tissue reaction." The term "tissue reaction" refers to a point at which intra-cellular and/or extra-cellular fluid begins to boil and/or vaporize, resulting in an increase in tissue impedance. In the case when the maximum allowable current value is reached, the maximum current value is maintained until the tissue reacts.

When the tissue reacts, the tissue treatment algorithm transitions to the impedance control phase. In the impedance control phase, the tissue treatment algorithm first calculates a target tissue impedance curve or trajectory and a target rate of change of tissue impedance (dZ/dt). Then, the tissue treatment algorithm controls the power level of the electrosurgical energy output from the generator so that the measured tissue impedance as measured according to the systems and methods of the present disclosure tracks the target tissue impedance trajectory and the target rate of change of tissue impedance.

Figure 8:
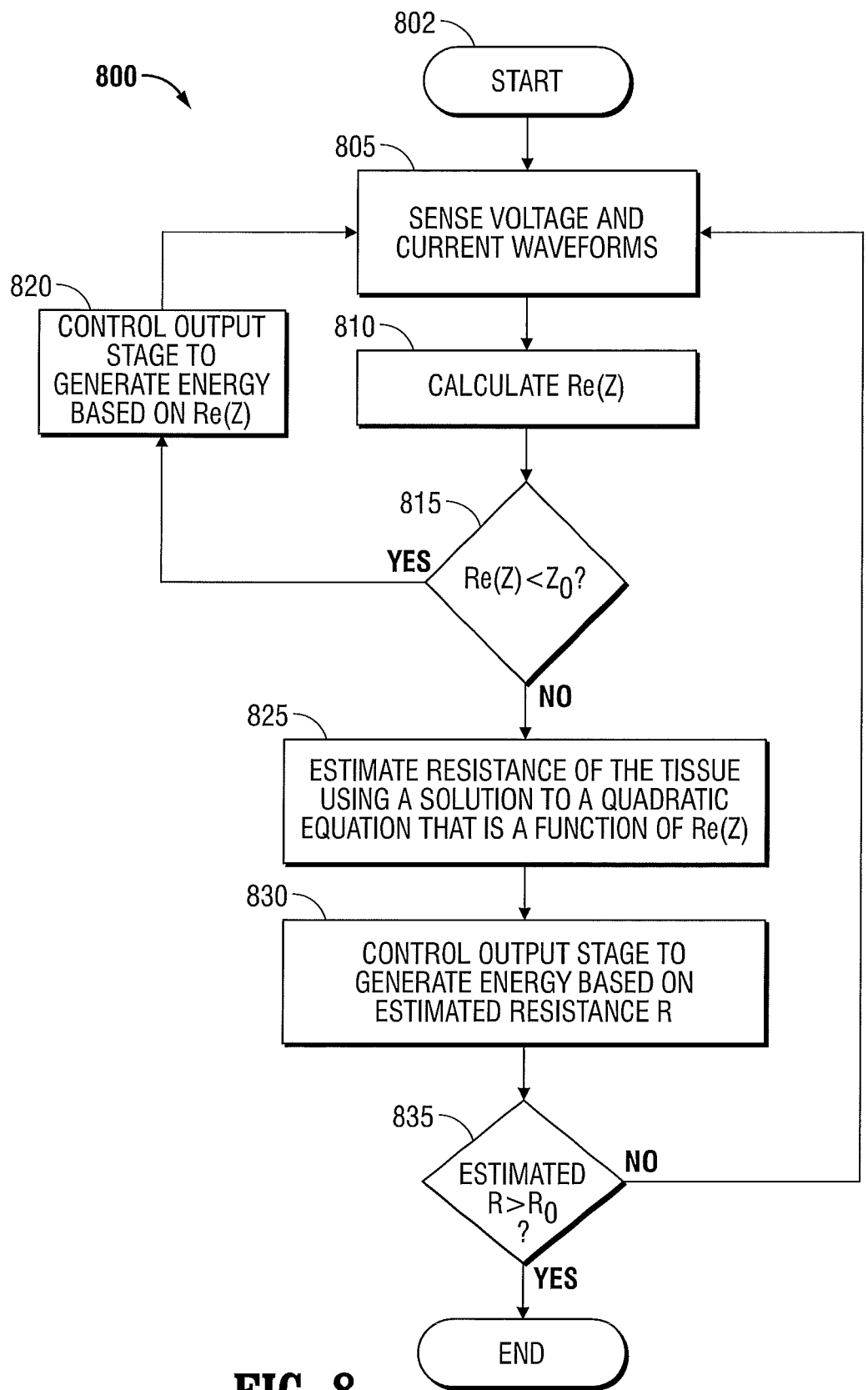
FIGS. 8 and 9 are flow diagrams of methods of controlling the output stage of the generator to compensate for the impedance of an electrosurgical cable according to embodiments of the present disclosure.

FIG. 8 illustrates a method 800 of controlling the output stage of the generator to compensate for parasitics in the electrosurgical cable during the impedance control phase. This method may be implemented in the DSP 235, which may be replaced by any suitable type of processor, of the electrosurgical generator 102 of FIG. 2. After the impedance control phase starts in step 802, the method 800 first involves sensing a voltage waveform and a current waveform of the generated electrosurgical energy in step 805. In step 810, a real part of an impedance is calculated based upon the sensed voltage and current waveforms. In step 815, it is determined whether the calculated impedance Re(Z) is less than a predetermined impedance value $Z_0$. The predetermined impedance value $Z_0$ represents an impedance threshold value near which the calculated real part of the impedance Re(Z) starts to deviate from the actual resistance of the tissue load.

If, in step 815, it is determined that the calculated real part of the impedance is less than the predetermined impedance value, then the output stage is controlled in step 820 to generate electrosurgical energy based on the calculated real part of the impedance. Then, the method 800 returns to step 805 to repeat the control process. If, in step 815, it is determined that the calculated real part of the impedance is not less than the predetermined impedance value, then, in step 825, a resistance of the tissue is estimated using a solution to a quadratic equation that is a function of the calculated real part of the impedance. Then, in step 830, a control signal for controlling the output stage is generated based on the estimated resistance of the tissue.

Next, in step 835, it is determined whether the estimated resistance of the tissue is greater than a predetermined tissue resistance $R_0$. If the estimated resistance of the tissue is greater than the predetermined tissue resistance $R_0$, then the method ends. Otherwise, the method 800 returns to step 805 to repeat the method 800.

Figure 9:
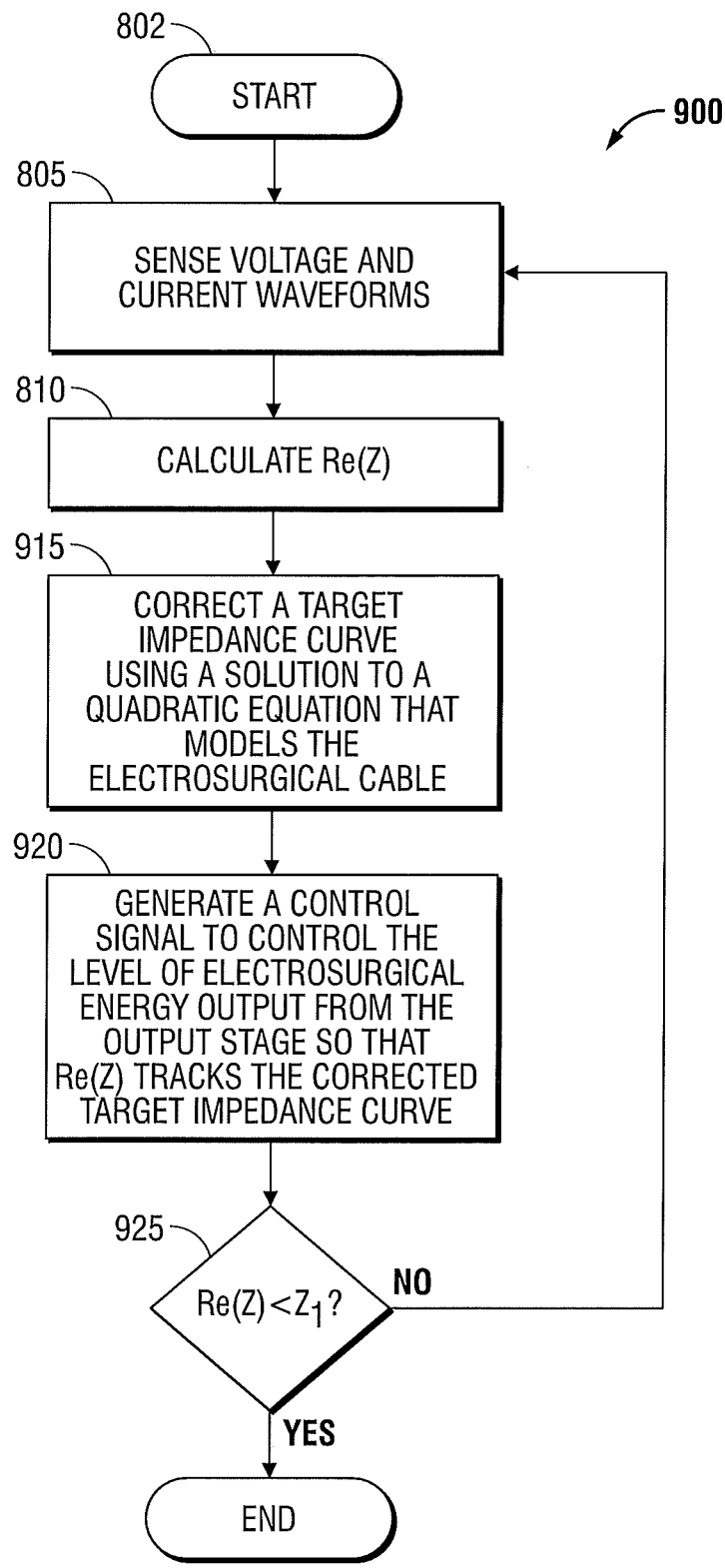

FIG. 9 illustrates another method 900 of controlling the output stage of the generator to compensate for parasitics in the electrosurgical cable. As in FIG. 8, after the impedance control algorithm starts in step 802, the voltage and current waveforms are sensed at the generator in step 805 and the real part of the impedance is calculated in step 810. Next, in step 915, the target impedance curve is corrected using a solution to a quadratic equation that models the electrosurgical cable as described above with respect to FIG. 6. Then, in step 920, a control signal is generated to control the level of electrosurgical energy output from the output stage so that the real part of the impedance tracks the corrected target impedance curve.

Next, in step 925, it is determined whether the real part of the impedance Re(Z) is greater than a predetermined impedance $Z_1$. If the real part of the impedance is greater than the predetermined tissue resistance $Z_1$, then the method ends. Otherwise, the method 900 returns to step 805 to repeat the method 900.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. An electrosurgical generator that delivers electrosurgical energy to tissue via a cable and an instrument coupled to the cable, the electrosurgical generator comprising:
   an output stage coupled to an electrical energy source and configured to generate electrosurgical energy;
   a plurality of sensors configured to sense a voltage waveform and a current waveform of the generated electrosurgical energy; and
   a controller configured to control the output stage, the controller comprising:
      a calculator configured to calculate a real part of an impedance based on the sensed voltage and current waveforms;
      an estimator configured to estimate a resistance of the tissue using a solution to a quadratic equation that is a function of a real part of the impedance; and
      a control signal generator configured to generate a control signal based on the estimated resistance of the tissue,
   wherein the solution to the quadratic equation is $$R_{load} = \frac{1 \pm \sqrt{1 - 4 \cdot (\omega \cdot C_{cable} \cdot \text{Re}(Z))^2}}{2 \cdot \text{Re}(Z) \cdot (\omega \cdot C_{cable})^2},$$

where $R_{load}$ is the estimated resistance of the tissue, $\omega$ is a frequency of the generated electrosurgical energy, $C_{cable}$ is a shunt capacitance of the cable connecting the electrosurgical generator to the instrument, and $\text{Re}(Z)$ is the real part of the impedance.

2. The electrosurgical generator according to claim 1, wherein the estimator uses the calculated real part of the impedance as the estimated resistance of the tissue when the calculated real part of the impedance is less than a predetermined value.

3. The electrosurgical generator according to claim 1, wherein the quadratic equation is derived from a model of the cable having a series inductor and a shunt capacitor.

4. The electrosurgical generator according to claim 3, wherein the estimated resistance of the tissue is a larger solution to the quadratic equation when a phase difference between the voltage waveform and the current waveform is less than or equal to −45 degrees, or a smaller solution when the phase difference is greater than −45 degrees.

5. The electrosurgical generator according to claim 1, further comprising a memory for storing a lookup table that maps a plurality of values of the real part of the impedance to a plurality of corresponding values of the estimated resistances of the tissue that are calculated according to a solution to the quadratic equation that is a function of the real part of the impedance,
   wherein the estimator estimates the resistance of the tissue by accessing the lookup table to determine the estimated resistance of the tissue corresponding to the calculated real part of the impedance.

6. The electrosurgical generator according to claim 5, wherein, when the calculated real part of the impedance is between two real parts of the impedance in the lookup table, the estimator selects the estimated resistance of the tissue corresponding the real part of the impedance in the lookup table that is nearest to the calculated real part of the impedance or interpolates between the two real parts of the impedance in the lookup table to determine the estimated resistance of the tissue.

7. The electrosurgical generator according to claim 1, further comprising a memory for storing a lookup table that maps a plurality of values of the real part of the impedance to a plurality of corresponding correction factors that are calculated based on a solution to the quadratic equation that is a function of the real part of the impedance,
   wherein the estimator estimates the resistance of the tissue by accessing the lookup table to determine a desired correction factor corresponding to the calculated real part of the impedance and multiplying the desired correction factor by the calculated real part of the impedance to obtain the estimated resistance of the tissue.

8. The electrosurgical generator according to claim 1, wherein the estimator estimates the resistance of the tissue using a polynomial equation that is determined by performing a polynomial curve fit to the solution to the quadratic equation that is a function of the real part of the impedance.

9. The electrosurgical generator according to claim 1, further comprising an inductor coupled to the output stage and tuned to a shunt capacitance and a series inductance of the cable so that the calculated real part of the impedance is sufficiently resistive.

10. The electrosurgical generator according to claim 9, wherein the shunt capacitance of the cable is a capacitance value measured when electrodes of the instrument are not in contact with tissue.

11. The electrosurgical generator according to claim 9, wherein an inductance value of the inductor is equal to $$\frac{1}{\omega^2 C_{cable}} - L_{cable},$$

where $\omega$ is a frequency of the generated electrosurgical energy, $C_{cable}$ is a shunt capacitance of the cable connecting the electrosurgical generator to the instrument, and $L_{cable}$ is a series inductance of the cable.

12. A method of controlling an electrosurgical generator that delivers electrosurgical energy to tissue via a cable and an instrument coupled to the cable, the method comprising:
   sensing a voltage waveform and a current waveform of the generated electrosurgical energy;
   calculating a real part of an impedance based on the sensed voltage and current waveforms;
   estimating a resistance of the tissue using a solution to a quadratic equation that is a function of a real part of the impedance; and
   generating a control signal to control the output from an output stage of the electrosurgical generator based on the estimated resistance of the tissue,
   wherein the solution to the quadratic equation is $$R_{load} = \frac{1 \pm \sqrt{1 - 4 \cdot (\omega \cdot C_{cable} \cdot \text{Re}(Z))^2}}{2 \cdot \text{Re}(Z) \cdot (\omega \cdot C_{cable})^2},$$

where $R_{load}$ is the estimated resistance of the tissue, $\omega$ is a frequency of the generated electrosurgical energy, $C_{cable}$ is a shunt capacitance of the cable connecting the electrosurgical generator to the instrument, and $\text{Re}(Z)$ is the real part of the impedance.

13. The method according to claim 12, further comprising:
   determining whether the calculated real part of the impedance is less than a predetermined value; and
   using the calculated real part of the impedance as the estimated resistance of the tissue when the calculated real part of the impedance is less than the predetermined value.

14. The method according to claim 12, further comprising using a larger solution to the quadratic equation as the estimated resistance of the tissue when a phase difference between the voltage waveform and the current waveform is smaller than or equal to −45 degrees, or using a smaller solution to the quadratic equation as the estimated resistance of the tissue when the phase difference is greater than −45 degrees.

15. The method according to claim 12, wherein the quadratic equation is derived from a model of the cable having a series inductor and a shunt capacitor.

16. The method according to claim 12, further comprising storing a lookup table that maps a plurality of values of the real part of the impedance to a plurality of corresponding values of the estimated resistances of the tissue that are calculated according to a solution to the quadratic equation that is a function of the real part of the impedance,
   wherein estimating the resistance of the tissue includes accessing the lookup table to determine the estimated resistance of the tissue corresponding to the calculated real part of the impedance.

17. The method according to claim 16, wherein, when the calculated real part of the impedance is between two real parts of the impedance in the lookup table, estimating the resistance of the tissue includes selecting the estimated resistance of the tissue corresponding the real part of the impedance in the lookup table that is nearest to the calculated real part of the impedance or interpolating between the two real part of the impedance in the lookup table to determine the estimated resistance of the tissue.

18. The method according to claim 12, further comprising storing a lookup table that maps a plurality of values of the real part of the impedance to a plurality of corresponding correction factors that are calculated based on a solution to the quadratic equation that is a function of the real part of the impedance,
   wherein the estimating the resistance of the tissue includes accessing the lookup table to determine a desired correction factor corresponding to the calculated real part of the impedance and multiplying the desired correction factor by the calculated real part of the impedance to obtain the estimated resistance of the tissue.

19. The method according to claim 12, wherein estimating the resistance of the tissue includes using a polynomial equation that is determined by performing a polynomial curve fit to the solution to the quadratic equation that is a function of the real part of the impedance.

20. A non-transitory computer-readable storage medium storing a program that, when executed a processor, performs a method of controlling an electrosurgical generator that delivers electrosurgical energy to tissue via a cable and an instrument coupled to the cable, the method comprising:
   sensing a voltage waveform and a current waveform of the generated electrosurgical energy;
   calculating a real part of an impedance based on the sensed voltage and current waveforms;
   estimating a resistance of the tissue using a solution to a quadratic equation that is a function of a real part of the impedance; and
   generating a control signal to control the output from an output stage of the electrosurgical generator based on the estimated resistance of the tissue,
   wherein the solution to the quadratic equation is $$R_{load} = \frac{1 \pm \sqrt{1 - 4 \cdot (\omega \cdot C_{cable} \cdot Re(Z))^2}}{2 \cdot Re(Z) \cdot (\omega \cdot C_{cable})^2},$$

where $R_{load}$ is the estimated resistance of the tissue, $\omega$ is a frequency of the generated electrosurgical energy, $C_{cable}$ is a shunt capacitance of the cable connecting the electrosurgical generator to the instrument, and $Re(Z)$ is the real part of the impedance.

* * * * *